United States Patent
Duff et al.

(10) Patent No.: US 6,476,219 B1
(45) Date of Patent: Nov. 5, 2002

(54) METHODS FOR PREPARING PHTHALOCYANINE COMPOSITIONS

(75) Inventors: James M. Duff, Mississauga (CA); James D. Mayo, Mississauga (CA); Roger E. Gaynor, Oakville (CA); Jeffrey H. Banning, Hillsboro, OR (US); Michael B. Meinhardt, Salem, OR (US); Randall R. Bridgeman, Hubbard, OR (US); Nan-Xing Hu, Oakville (CA); Carol A. Jennings, Toronto (CA); Marko D. Saban, Etobicoke (CA); Paul F. Smith, Oakville (CA); Hadi K. Mahabadi, Toronto (CA)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 10/072,237

(22) Filed: Feb. 8, 2002

(51) Int. Cl.⁷ .................. C07D 487/22; C07B 47/10
(52) U.S. Cl. .................. 540/128; 540/139; 540/140
(58) Field of Search .................. 540/128, 139, 540/140

(56) References Cited

U.S. PATENT DOCUMENTS

| | | | |
|---|---|---|---|
| 3,653,932 A | 4/1972 | Berry et al. | 106/22 |
| 3,674,494 A | 7/1972 | Hoffman et al. | 96/86 P |
| 4,390,369 A | 6/1983 | Merritt et al. | 106/31 |
| 4,484,948 A | 11/1984 | Merrit et al. | 106/31 |
| 4,684,956 A | 8/1987 | Ball | 346/1.1 |
| 4,851,045 A | 7/1989 | Taniguchi | 106/31 |
| 4,875,903 A | 10/1989 | Pedrazzi | 8/640 |
| 4,889,560 A | 12/1989 | Jaeger et al. | 106/27 |
| 4,889,761 A | 12/1989 | Titterington et al. | 428/195 |
| 5,006,170 A | 4/1991 | Schwarz et al. | 106/20 |
| 5,149,800 A | 9/1992 | Kluger et al. | 540/123 |
| 5,151,120 A | 9/1992 | You et al. | 106/27 |
| 5,221,335 A | 6/1993 | Williams et al. | 106/23 A |
| 5,280,114 A | 1/1994 | Itoh et al. | 540/122 |
| 5,372,852 A | 12/1994 | Titterington et al. | 427/288 |
| 5,496,879 A | 3/1996 | Griebel et al. | 524/320 |
| 5,621,022 A | 4/1997 | Jaeger et al. | 523/161 |
| 5,847,114 A | 12/1998 | Thetford et al. | 540/140 |
| 6,087,492 A | * 7/2000 | Wolleb | 540/139 |

FOREIGN PATENT DOCUMENTS

| | | |
|---|---|---|
| DE | 4205636 AL | 8/1993 |
| DE | 4205713 Al | 3/1996 |
| EP | 0 187 352 A2 | 7/1986 |
| EP | 0 206 286 A1 | 12/1986 |
| EP | 0 209 487 A2 | 9/1987 |
| EP | 0 540 953 A2 | 5/1993 |
| EP | 0 398 716 B1 | 1/1996 |
| EP | 0 787 732 A2 | 8/1997 |
| EP | 0 714 954 A2 | 1/1998 |
| EP | 1 013 721 A2 | 6/2001 |
| JP | 58196295 | 11/1983 |
| JP | 61146597 | 7/1986 |
| JP | 62111249 | 3/1990 |
| JP | 5086301 | 4/1993 |
| JP | 5222302 | 8/1993 |
| JP | 8225751 | 9/1996 |
| JP | 8302224 | 11/1996 |
| JP | 9279050 | 10/1997 |
| WO | WO 94/04619 | 3/1994 |
| WO | 0 742 255 A1 | 11/1996 |
| WO | WO 98/14520 | 4/1998 |

OTHER PUBLICATIONS

W.E. Ford et al.; Synthesis and Photochemical Properties of Aluminum, Gallium, Silicon, and Tin Naphthalocyanines; Inorg. Chem., 31 (1992), 3371.

B.L. Wheeler et al.; A Silicon Phthalocyanine and a Silicon Naphthalocyanine: Synthesis, Electrochemistry, and Electrogenerated Chemiluminescence; J. Am. Chem. Soc., 106 (1984), 7404.

K.L. Wooley et al.; Hyperbranched Macromolecules via a Novel Double–Stage Convergent Growth Approach; J. Am. Chem. Soc. 113 (1991), 4252.

M.A. Hanack; Snythesis and Properties of Conducting Bridged Macrocyclic Metal Complexes; Molecular Crystals and Liquid Crystals, 105 (1984), 133.

(List continued on next page.)

Primary Examiner—Bruck Kifle
(74) Attorney, Agent, or Firm—Judith L. Byorick

(57) ABSTRACT

Disclosed is a process for preparing a colorant of the formula

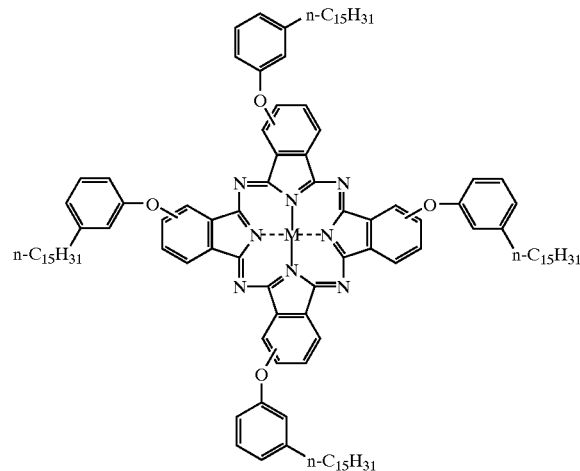

wherein M is an atom or group of atoms capable of bonding to the central cavity of a phthalocyanine molecule, wherein axial ligands optionally can be attached to M, which comprises (a) reacting 3-n-pentadecylphenol with 4-nitrophthalonitrile in the presence of a base to form an alkylarylether adduct of phthalonitrile; and (b) reacting the alkylarylether adduct of phthalonitrile with either (i) a metal compound, or (ii) an ammonia-releasing compound in the presence of an alkanolamine solvent, or (iii) mixtures of (i) and (ii), to form the colorant.

52 Claims, No Drawings

OTHER PUBLICATIONS

F. Cariati; New Adducts of Phthalocyaninatocobalt(II) with Pridine and 4–Methyl–pyridine and their Vibrational, Magnetic, and Electronic Proeprties. Part I. Reactivity toward Oxygen; J. Chem. Soc. Dalton Trans (1975), 556.

S.A. Mikhalenko et al.; Phthalocyanine and Related Compounds IX. Synthesis and Electronic Absorption Spectra of Tetra–4–t–Butylphtalocyanines; Zhur. Obschei Khimii, 41 (1971), 2375.

S.M. Marcuccio et al.; Binuclear phthalocyanines convalently linked through two–and four–atom bridges; Can. J. Chem., 63 (1985), 3957.

N.B. McKeown et al.; Lyotropic and Thermotropic Mesophase Formation of Novel Tetra–[oligo(ethyleneoxy)]– substituted Phthalocyanines; J. Materials Chem., 4(1994), 1153.

R. E. Wyant; German Offenlegungsschrift; 2,224,063 (1973).

K. Ogawa; Highly Ordered Monolayer Assemblies of Phthalocyanine Derivatives; J. Am. Chem. Soc. Chem. Comm., (1989), 477.

M. Fujiki et al.; Self–Assembling Features of Soluble Nickel Phthalocyanines; J. Phys. Chem. 9 (1988), 1281.

M. Sommerauer et al.; Separation of 2(3), 9(10), 16(17), 23(24)–Tetrasubstituted Phthalcyanines with Newly Developed HPLC Phases; J. Am. Chem. Soc., vol. 118, No. 42, p. 10085 (1996).

J.G. Young et al.; Synthesis and Characterization of Di–d–isubstituted Phthalocyanines; J. Org. Chem., vol. 55, No. 7, P. 2155 (1990).

A. Sastre et al.; Synthesis of Novel Unsymmetrically Substituted Push–Pull Phthalocyanines; J. Org. Chem., vol. 61, No. 24, P. 8591 (1996).

D.M. Drew et al.; The Synthesis of Pure 1, 11, 15,25–Tetrasubstituted phthalocyanines as Single Isomers Using Bisphthalonitriles; Synlett, 1994 (Ang), p. 623.

K. Ohta et al.; Annelides XXIX, Influence of the nature of the side–chains on the mesomorphic properties of octasubstituded phthalocyanine derivatives; New J. Chem., 12 (1988) 751.

N.B. McKeown et al.; Synthesis and Characterisation of some 1,4,8,11 15, 18,22,25–Octa–alkyl–and 1,48, 11, 15, 18–Hexa–alkyl–22–25–bis(carboxyproply)phthalocyanines; J. Chem. Soc. Perkin Trans., 1 (1990), 1169.

E. Orthmann et al.; Preparation of Ultrathin Layers of Molecularity Controlled Architecture from Polymeric Phthalocyanines by the Langmuir–Blodgett–Technique; Angew. Chem. Int. Ed. Engl. 25 (1986), 1105.

A.N. Cammidge et al.; Synthesis and Characterisation of some 1,4,8,11 15,18,22,25–Octa–alkyl–and 1,4,8,11, 15,18–Hexa–alkyl–22–25–bis(carboxypropyl)phthalocyanines; J. Chem. Soc. Perkin Trans., 1 (1991), 3053.

C. Piechoki et al.; Synthesis of a Polar Discogen. A New Type of Discotic Mesophase; Chem. Comm. (1985, 259.

M.J. Cook et al.; Octa–alkoxyphthalocyanine and naphtalocyanine derivatiives: dyes with Q–band absorption in the far red or near infrared; Chem. Soc. Perkin Trans., 1 (1988), 2453.

N. Kobayashi et al.; Symmetrically Tetra–substituted Phthalocyanines; J. Chem. Soc. Chem. Comm. (1987), 390.

P.J. Brach et al.; Improved Synthesis of Metal–free Phthalocyanines; Heterocyclic Chem., 7 (1970), 1403.

J.A. Thompson et al.; Synthesis of High–Purity Phthalocyanines (pc): High Intrinsic Conductivities in the Molecular Conductors $H_2$ (pc)I and Ni(pc)I.

R.A. McClelland et al.; Kinetics and equilibrium in the ammonolysis of substituted phthalimides; Can. J. Chem., 63(1985), 121.

M.J. Cook et al.; 1,4,8, 11, 15, 1–Hexa–alkyl–22,225–bis-(carboxypropyl)phthalocyanines: Materials designed for Deposition as Langmui–Blodgett Films; J. Chem. Soc. Chem. Comm. (1987), 1148.

\* cited by examiner

METHODS FOR PREPARING PHTHALOCYANINE COMPOSITIONS

Copending application U.S. Ser. No. 10/072,241, filed concurrently herewith, entitled "Phthalocyanine Compositions," with the named inventors Jeffery H. Banning, Nan-Xing Hu, James D. Mayo, James M. Duff, Roger E. Gaynor, Rosa M. Duque, and Nam S. Ro, the disclosure of which is totally incorporated herein by reference, discloses compounds of the formula

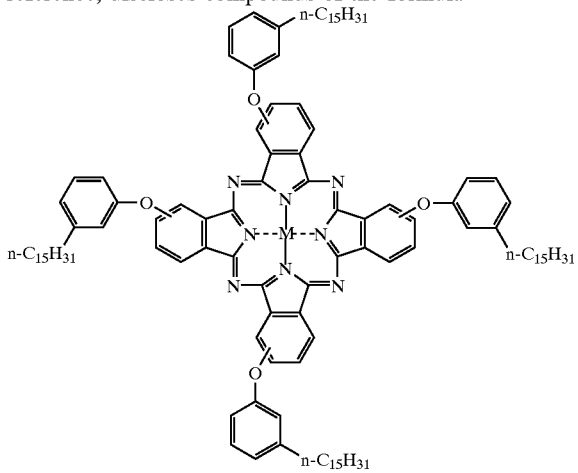

wherein M is an atom or group of atoms capable of bonding to the central cavity of a phthalocyanine molecule, wherein axial ligands optionally can be attached to M.

Copending application U.S. Serial No. 10/072,210, filed concurrently herewith, entitled "Ink Compositions Containing Phthalocyanines," with the named inventors Donald R. Titterington, Michael B. Meinhardt, Jeffery H. Banning, James D. Mayo, James M. Duff, Roger E. Gaynor, and Harold R. Frame, the disclosure of which is totally incorporated herein by reference, discloses a phase change ink composition comprising a phase change ink carrier and a colorant compound of the formula

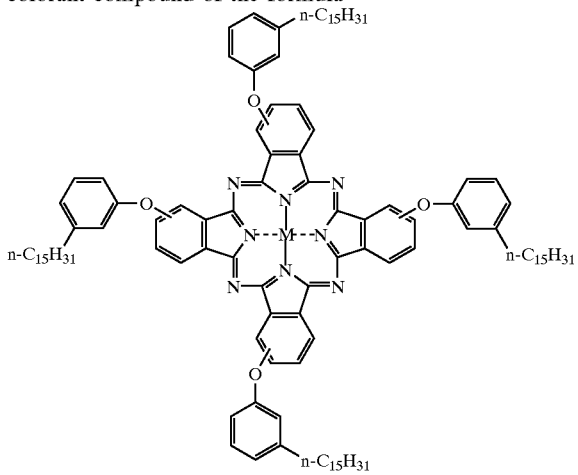

wherein M is an atom or group of atoms capable of bonding to the central cavity of a phthalocyanine molecule, wherein axial ligands optionally can be attached to M. Also disclosed are printing processes using the phase change inks.

BACKGROUND OF THE INVENTION

The present invention is directed to methods for preparing colorant compounds. More specifically, the present invention is directed to processes for preparing phthalocyanine colorant compounds particularly suitable for use in hot melt or phase change inks. One embodiment of the present invention is directed to a process for preparing a colorant of the formula

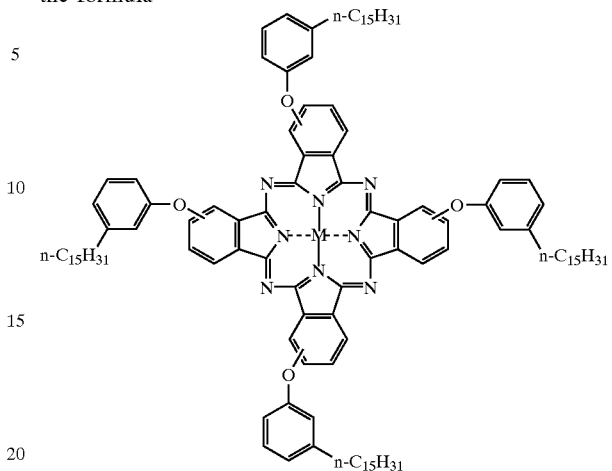

wherein M is an atom or group of atoms capable of bonding to the central cavity of a phthalocyanine molecule, wherein axial ligands optionally can be attached to M, which comprises (a) reacting 3-n-pentadecylphenol with 4-nitrophthalonitrile in the presence of a base to form an alkylarylether adduct of phthalonitrile; and (b) reacting the alkylarylether adduct of phthalonitrile with either (i) a metal compound, or (ii) an ammonia-releasing compound in the presence of an alkanolamine solvent, or (iii) mixtures of (i) and (ii), to form the colorant.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. Nos. 4,889,560, 4,889,761, and 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking and industrial marking and labelling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. Nos. 3,653,932, 4,390,369, 4,484,948, 4,684,956, 4,851,045, 4,889,560, 5,006,170, 5,151,120, 5,372,852, 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

Colorants suitable for hot melt or phase change ink compositions include members of the phthalocyanine class of chromophore which have been appropriately modified by chemical substitution to make them soluble in the organic carrier composition. Many such phthalocyanine derivatives are known to have a good cyan color, and absorb light strongly in the wavelength region of from about 600 to about 700 nanometers. Further, their well-known high chemical, thermal, and photochemical stability make them particularly attractive for printing applications where archival print properties are desired. Most phthalocyanines soluble in organic media fall into three generic classes: axially-substituted phthalocyanines, tetra-peripherally-substituted phthalocyanines, and octa-peripherally-substituted phthalocyanines.

The first class is illustrated by the following structure:

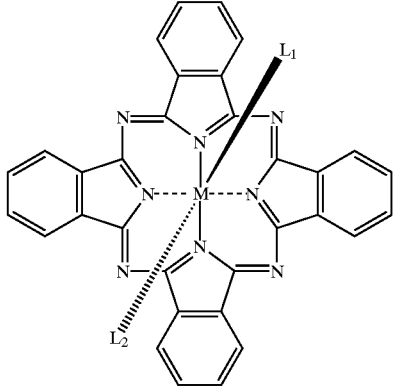

In the most well-known examples of this class, M is tetravalent silicon, germanium, or tin and $L_1$ and $L_2$ can each be either bulky alkylsiloxy groups, such as —OSiR$_3$ (wherein R is, for example, n-hexyl) or long-chain oxyhydrocarbon groups. See, for example, "Synthesis and photochemical properties of aluminum, gallium, silicon and tin naphthalocyanines," W. E. Ford, M. A. Rodgers, L. A. Schechtman, J. R. Sounik, B. D. Rihter, and M. E. Kenney, *Inorg. Chem.*, 31 (1992), 3371;"A silicon phthalocyanine and a silicon naphthalocyanine: synthesis, electrochemistry, and electrically-generated chemiluminescence," B. L. Wheeler, G. Nagasubramanian, A. J. Bard, L. A. Schechtman, and M. E. Kenney, *J. Am. Chem. Soc.*, 106 (1984), 7404;the disclosures of each of which are totally incorporated herein by reference. Also reported are examples in which M=Si and $L_1$ and $L_2$ are dendritic groups; see, for example, "Hyperbranched macromolecules via a novel double-stage convergent growth approach," K. L. Wooley, C. J. Hawker, and J. M. J. Frechet, *J. Am. Chem. Soc.*, 113 (1991), 4252, the disclosure of which is totally incorporated herein by reference. A special class of such molecules are those in which M is a divalent transition metal, such as iron, cobalt, zinc, or ruthenium, and $L_1$ and $L_2$ are neutral coordinating ligands, such as pyridine, quinoline, or 1,4-diazabicyclo[2,2,2]octane; see, for example, "Synthesis and properties of conducting bridged macrocyclic metal complexes," M. A. Hanack, *Molecular Crystals and Liquid Crystals*, 105 (1984), 133;"New adducts of phthalocyanine cobalt(II) with pyridine and 4-methylpyridine and their vibrational, magnetic and electronic properties I. Reactivity towards oxygen," F. Cariati, D. Galizzioli, F. Morazzoni, and C. Busetto, *J. Chem. Soc., Dalton Trans.* (1975), 556, the disclosures of each of which are totally incorporated herein by reference.

Peripherally tetrasubstituted phthalocyanines soluble in organic media are also known. Substituents can be either at the 2- (or 3-) positions, or at the 1- (or 4-) positions, as illustrated below, and typically are bulky (e.g. tertiary-alkyl) or contain long alkyl chains (e.g., more than about five carbons):

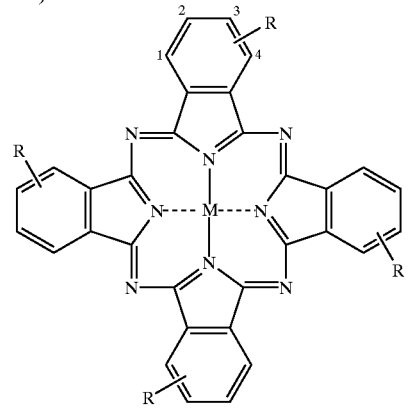

Some reported examples of R-groups conferring solubility are tert-butyl ("Phthalocyanines and related compounds IX. Synthesis and electronic absorption spectra of tetra-t-butylphthalocyanines," S. A. Mikhalenko, S. V. Barknova, O. L. Lebedev, and E. A. Luk'yanets, *Zhur. Obschei Khimii*, 41 (1971), 2375, the disclosure of which is totally incorporated herein by reference), neopentyloxy ("Binuclear phthalocyanines covalently linked through two-atom and four-atom bridges," S. M. Marcuccio, P. I. Svirskaya, S. Greenberg, A. B. P. Lever, C. C. Leznoff, and K. B. Tomer, *Can. J. Chem.*, 63 (1985), 3957, the disclosure of which is totally incorporated herein by reference), 4-cumylphenoxy ("Molecular association and monolayer formation of soluble phthalocyanine compounds," A. W. Snow and N. L. Jarvis, *J. Am. Chem. Soc.*, 106 (1984), 4706, the disclosure of which is totally incorporated herein by reference), oligo (ethyleneoxy) ("Lyotropic and thermotropic mesophase formation of novel tetra[oligo(ethyleneoxy)]-substituted phthalocyanines," N. B. McKeown and J. Painter, *J. Materials Chem.*, 4 (1994), 1153, the disclosure of which is totally incorporated herein by reference), long-chain alkysulfamoyl, RNHSO$_2$— (R. E Wyant, German Offenlegungsschrift, 2,224,063 (1973), the disclosure of which is totally incorporated herein by reference), long-chain alkyl carboxylate, ROCO— ("Highly ordered monolayer assemblies of phthalocyanine derivatives," K. Ogawa, S. Kinoshita, H. Yonehara, H. Nakahara, and F. Fukuda, *J. Am. Chem. Soc. Chem. Comm.*, (1989), 477, the disclosure of which is totally incorporated herein by reference), and long-chain alkyl carboxamide, RNHCO— ("Self-assembling features of soluble nickel phthalocyanines," M. Fujiki, H. Tabei, and T. Kurihara, *J. Phys. Chem.* 9 (1988), 1281, the disclosure of which is totally incorporated herein by reference).

A common feature of all such tetrasubstituted phthalocyanines is that they are obtained as a mixture of four constitutional isomers resulting from statistical cyclotetramerization of four isoindolenine units ("Synthesis and Chromatographic separation of tetrasubstituted and Unsymmetrically substituted phthalocyanines," G. Schmid, M. Sommerauer, M. Geyer, and M. Hanack, in *Phthalocyanines—Properties and Applications*, C. C. Leznoff and A. B. P. Lever, Editors, Volume 4, Chapter 1, the disclosure of which is totally incorporated herein by reference). These isomers, which are named according to their symmetry space group as C4h, D2h, C2v and Cs, are illustrated below:

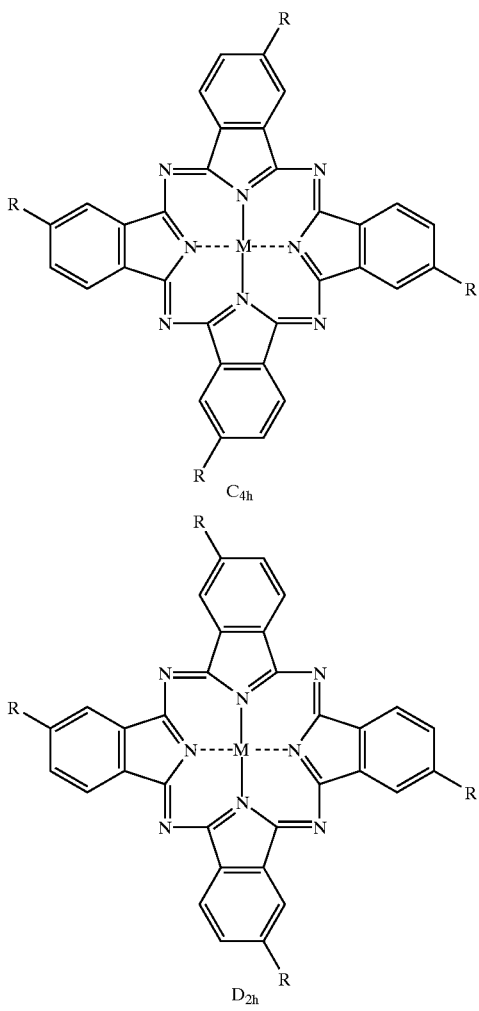

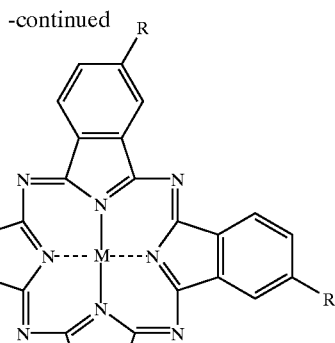

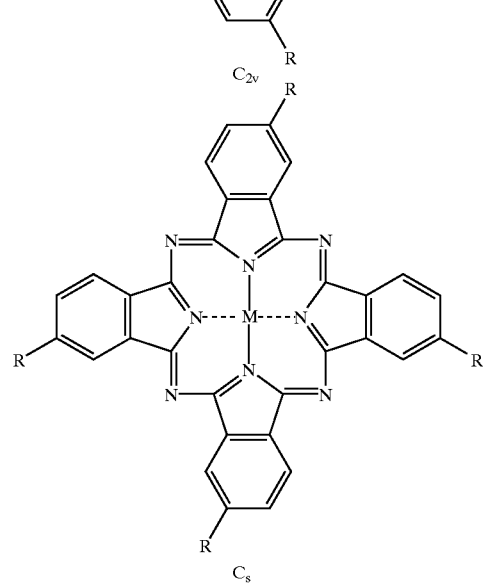

Statistical synthesis would give these four isomers in a ratio of 1:1:2:4, respectively. This phenomenon is described in more detail in "Separation of 2(3),9(10),16(17),23(24)-Tetrasubstituted Phthalocyanines with Newly Developed HPLC Phases," M. Sommerauer, C. Rager, and M. Hanack, *J. Am. Chem. Soc.*, Vol. 118, No. 42, p. 10085 (1996), the disclosure of which is totally incorporated herein by reference, which discloses the synthesis of 2(3),9(10),16 (17),23(24)-tetrasubstituted phthalocyanines from 1,2-dicyano-4-alkoxybenzenes or the corresponding isoindolines. In each case, four isomers with $D_{2h}$, $C_{4h}$, $C_{2v}$, and $C_s$ symmetry were obtained in the statistically expected yield. The separation of the $C_{4h}$ and the $D_{2h}$ isomers was achieved successfully for the first time from the other two isomers with newly developed HPLC phases based on π-π interactions. In one case, a particular phthalocyanine could be separated into four different isomers and characterized by UV/VIS and $^1$H-NMR spectroscopy.

All four R groups in the class of tetrasubstituted phthalocyanines need not be identical. When two, differently-substituted, precursors are cyclotetramerized to form phthalocyanine, a mixture of six different isomers are possible ("Synthesis and Chromatographic separation of tetrasubstituted and Unsymmetrically substituted phthalocyanines," G. Schmid, M. Sommerauer, M. Geyer, and M. Hanack, in *Phthalocyanines— Properties and Applications,* C. C. Leznoff and A. B. P. Lever, Editors, Volume 4, Chapter 1, the disclosure of which is totally incorporated herein by reference). By using specially designed intermediates, it is possible to control the number of possible isomers. For example, "Synthesis and Characterization of Di-disubstituted Phthalocyanines," J. G. Young and W. Onyebuagu, *J. Org. Chem.*, Vol. 55, No. 7, p. 2155 (1990), the disclosure of which is totally incorporated herein by reference, discloses an improved approach to the synthesis of di-disubstituted phthalocyanines from two different phthalyl precursors wherein the resultant product contains two different R-groups. The method can be applied to the synthesis of hydrogen and metallo phthalocyanine. The yields are variable, ranging from 17 percent to 72 percent, depending on the substituents. Tetra-substituted phthalocyanines having different R groups are also described in "Synthesis of Novel Unsymmetrical Substituted Push-Pull Phthalocyanines," A. Sastre, B. del Rey, and T. Torres, *J. Org. Chem.*, Vol. 61, No. 24, p. 8591 (1996), the disclosure of which is totally incorporated herein by reference. This paper discloses the synthesis and characterization of novel, non-centrosymmetrically, push-pull substituted metal-free phthalocyanines. The compounds had different donor (dialkoxy, tert-butyl, methyl, p-tolylthio) and/or attractor (p-tolylsulfinyl, p-tolylsulfonyl, nitro) functional groups, were soluble in organic solvents, and were especially designed to study their second- and third-order nonlinear optical properties.

It is also possible, in certain cases, to obtain the 1(4) tetrasubstituted phthalocyanines as single isomers, as described in "The Synthesis of Pure 1,11,15,25-tetrasubstituted Phthalocyanines as Single Isomers Using Bisphthalonitriles," D. M. Drew and C. C. Leznoff, *Synlett*, 1994 (Ang), p. 623, the disclosure of which is totally incorporated herein by reference. This paper discloses bisphthalonitriles linked by 2,2-disubstituted propan-1,3-diol precursors which gave pure 1,11,15,25-substituted isomers of mononuclear phthalocyanine derivatives upon homocyclization. Reasonable yields of these phthalocyanines could be obtained with limited polymeric side-products utilizing modified cyclization methods. The $^1$H NMR spectrum of these phthalocyanines exhibited the discrete doublet-triplet-doublet proton signals expected of a pure isomer.

The third generic class of phthalocyanines soluble in common organic solvents is the peripherally octa-substituted compounds illustrated below. The substituents can occupy either the 1,4- or the 2,3-positions. These compounds are generally obtained as a single isomer. The solubility in a given solvent is related to the nature and chain length of the R group, with more than about five carbon atoms per chain being typical:

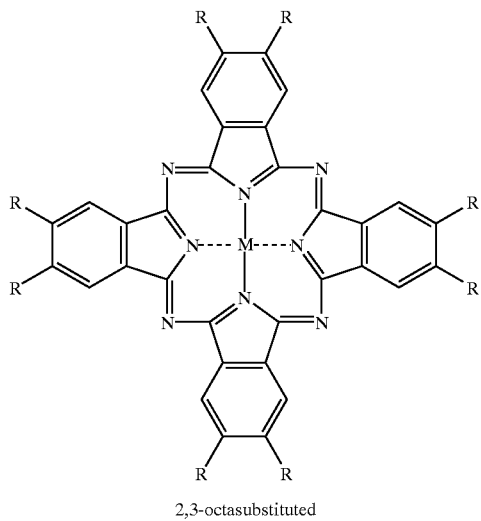

2,3-octasubstituted

-continued

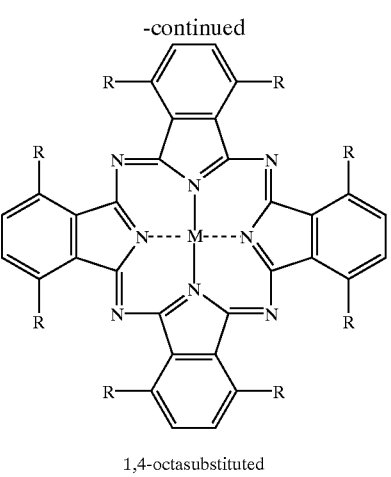

1,4-octasubstituted

Many examples have been reported for this class: 2,3-alkyl ("Annelides XXIX. Influence of the nature of the side-chains on the mesomorphic properties of octasubstituted phthalocyanine derivatives," K. Ohta, L. Jacquemin, C. Sirlin, L. Bosio, and J. Simon, *New J. Chem.*, 12 (1988), 751, the disclosure of which is totally incorporated herein by reference), 1,4-alkyl ("Synthesis and characterization of some 1,4,8,11,15,18,22,25-octaalkylphthalocyanines and 1,4,8,11,15,18,-hexaalkyl-22,25-bis(carboxypropyl) phthalocyanines," N. B. McKeown, I. Chambrier, and M. J. Cook, *J. Chem. Soc. Perkin Trans.*, 1 (1990), 1169, the disclosure of which is totally incorporated herein by reference), 2,3-alkoxy ("Preparation of ultrathin layers of molecularly controlled architecture from polymeric phthalocyanines by the Langmuir-Blodgett technique," E. Orthmann and G. Wegner, *Angew. Chem. Int. Ed. Engl.*, 25 (1986), 1105, the disclosure of which is totally incorporated herein by reference), 1,4-alkoxy ("Synthesis and characterization of some 1,4,8,11,15,18,22,25-octa(alkoxymethyl) phthalocyanines: a new series of discotic liquid crystals," A. N. Cammidge, M. J. Cook, K. J. Harrison, and N. B. McKeown, *J. Chem. Soc. Perkin Trans.*, 1 (1991), 3053, the disclosure of which is totally incorporated herein by reference), 2,3-alkoxymethylene ("A convenient synthesis of octasubstituted phthalocyanines," G. Pawlowski and M. Hanack, Synthesis (1980), 287; "Synthesis of a polar discogen. A new type of discotic mesophase," C. Piechoki and J. Simon, *Chem. Comm.* (1985), 259, the disclosures of each of which are totally incorporated herein by reference), 1,4-alkoxymethylene (Octa-alkoxyphthalocyanine and naphthalocyanine derivatives: dyes with Q-band absorption in the far red or near infrared," M. J. Cook, A. J. Dunn, S. D. Howe, A. J. Thomson, and K. J. Harrison, *J. Chem. Soc. Perkin Trans.*, 1 (1988), 2453, the disclosure of which is totally incorporated herein by reference), and 2,3-alkyldicarboximide (N. Kobayashi, Y. Nishiyama, T. Oya, and M. Sato, *J. Chem. Soc. Chem. Comm.*, (1987), 390, the disclosure of which is totally incorporated herein by reference). Many of the compounds in this class exhibit liquid crystalline behavior as discussed in "Phthalocyanine-Based Liquid Crystals: Towards Submicronic Devices," J. Simon and P. Bassoul, Chapter 6, Volume 4 of *Phthalocyanines-properties and Applications*, C. C. Leznoff and A. B. P. Lever (VCH Publishers Inc. N. Y.), the disclosure of which is totally incorporated herein by reference.

Substituted metal phthalocyanines may be prepared by, for example, the cyclotetramerization, generally in a high boiling solvent, of suitable precursors in the presence of a metal salt. Suitable precursors are substituted phthalonitriles, 1,3-diiminoisondolines, orthocyanobenzamide, phthalic anhydrides, and phthalimides. With the latter two precursors, a source of ammonia such as urea is provided to obtain phthalocyanine (F. H. Moser and A. L. Thomas, "The Phthalocyanines. Volume 1, Properties," CRC Press, 1983, the disclosure of which is totally incorporated herein by reference). Metal-free phthalocyanine can be obtained by, for example, refluxing phthalonitrile with ammonia gas in 2-N,N-dimethylaminoethanol (P. J. Brach, S. J. Grammatica, O. A. Ossanna, and I. Weinberger, *J. Heterocyclic Chem.*, 7 (1970), 1403, the disclosure of which is totally incorporated herein by reference), by the condensation of phthalonitrile in hydroquinone solvent (J. A. Thompson, K. Murata, D. C. Miller, J. L. Stanton, W. E. Broderick, B. M. Hoffmann, and J. A Ibers, *Inorganic Chem.*, 32 (1993), 3546, the disclosure of which is totally incorporated herein by reference), or by the treatment of dilithium phthalocyanine with acid (N. B. McKeown, I. Chambrier, and M. J. Cook, *J. Chem. Soc. Perkin Trans.*, 1, (1990), 1169, the disclosure of which is totally incorporated herein by reference).

Some suitable precursors for synthesis of substituted phthalocyanines, such as 3- and 4-substituted phthalic anhydrides, phthalimides, and phthalonitriles, are commercially available (see, for example, Sigma-Aldrich Company's *Handbook of Fine Chemicals and Laboratory Equipment*, the disclosure of which is totally incorporated herein by reference). Others can be prepared by, for example, oxidation of substituted ortho-xylenes ("Phthalocyanines and related compounds IX. Synthesis and electronic absorption spectra of tetra-t-butylphthalocyanines," S. A. Mikhalenko, S. V. Barknova, O. L. Lebedev, and E. A. Luk'yanets, *Zhur. Obschei Khimii*, 41 (1971), 2375;"Kinetics and equilibrium in the ammonolysis of substituted phthalimides," R. A. McClelland, N. E. Seaman, J. M. Duff, and R. E. Branston, *Can. J. Chem.*, 63 (1985), 121, the disclosures of each of which are totally incorporated herein by reference), treatment of substituted ortho-dibromobenzenes with copper cyanide ("Synthesis of substituted o-phthalonitriles by the Rosemund von Braun reaction," E. I. Kovshev, L. I. Solov'eva, S. A. Mikhalenko, and E. A. Luk'yanets, *Mendeleev Chemistry Journal*, 21 (1976), 465, the disclosure of which is totally incorporated herein by reference) by reaction of the 4-nitrophthalonitrile with alkoxide or aryloxide ion ("Binuclear phthalocyanines covalently linked through two-atom and four-atom bridges," S. M. Marcuccio, P. I. Svirskaya, S. Greenberg, A. B. P. Lever, C. C. Leznoff, and K. B. Tomer, *Can J. Chem.* 63 (1985), 3957; "Molecular association and monolayer formation of soluble phthalocyanine compounds," A. W. Snow and N. L. Jarvis, *J. Am. Chem. Soc.* 106 (1984), 5706, the disclosures of each of which are totally incorporated herein by reference), or by the Diels-Alder reaction of substituted furans with fumaronitrile ("1,4,8,11,15,18-hexaalkyl-22,25-bis(carboxypropyl) phthalocyanines: materials designed for deposition as Langmuir-Blodgett films," M. J. Cook, M. F. Daniel, K. J. Harrison, N. B. McKeown, and A. J. Thompson, *J. Chem. Soc. Chem. Comm.*, (1987), 1148, the disclosure of which is totally incorporated herein by reference).

The above discussion is a brief summary of a large volume of published work related to soluble phthalocyanines. It is intended to be illustrative rather than comprehensive. Further information can be obtained from the following three textbooks: *The Phthalocyanines,* Volumes 1 and 2, by F. H. Moser and A. L. Thomas (CRC Press, 1983); *Phthalocyanines—Properties and Applications,* Volumes 1 to 4, by C. C. Leznoff and A. B. P. Lever (VCH Publishers, Inc., 1993); *Phthalocyanine Materials,* by N. B. McKeown (Cambridge University Press, 1998); and references cited therein, the disclosures of each of which are totally incorporated herein by reference.

U.S. Pat. No. 5,847,114 (Thetford et al.), the disclosure of which is totally incorporated herein by reference, discloses the use of substituted phthalocyanines for the generation of singlet oxygen in which at least one of the peripheral carbon atoms in the 1–16 positions of the phthalocyanine nucleus (MκPc) of Formula:

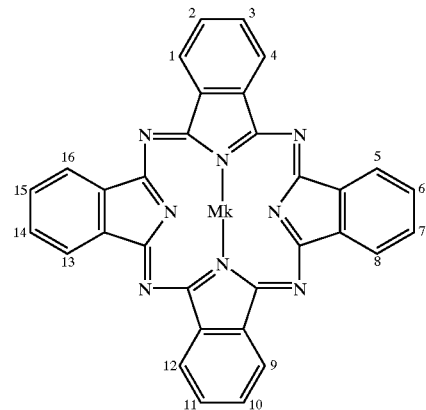

wherein M is selected from H, metal, halometal, oxymetal, and hydroxymetal, and k is the inverse of 1/2 of the valency of M; is linked via an oxygen atom to an aromatic radical and the remaining peripheral carbon atoms are unsubstituted or substituted by any combination of atoms or groups and sulfonated derivatives thereof, provided that the phthalocyanine absorbs electromagnetic radiation at a wavelength from 650 nanometers to 800 nanometers.

U.S. Pat. No. 5,280,114 (Itoh et al.), the disclosure of which is totally incorporated herein by reference, discloses halogenated alkoxyphthalocyanine having a controlled grade of halogenation that can be prepared by reacting a single compound or a mixture of phthalocyanine represented by the formula:

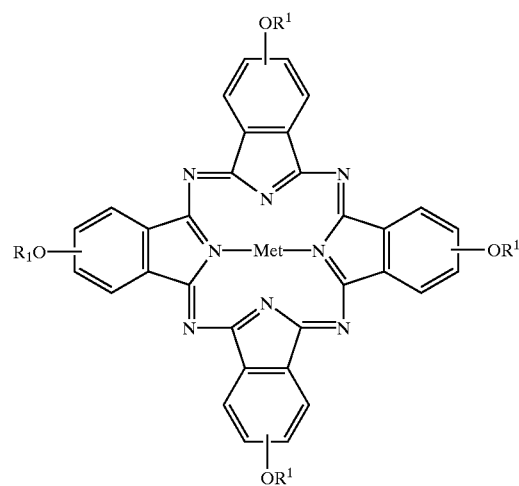

wherein $R^1$ is a substituted or unsubstituted alkyl group and may be the same or different, and Met is two hydrogen atoms, a divalent metal atom, or a trivalent or tetravalent metal derivative, with 1 to 6 mole ratio of a halogenating agent at 0° to 260° C. in a solvent of from 1 to 1000 times by weight.

U.S. Pat. No. 5,149,800 (Kluger et al.), the disclosure of which is totally incorporated herein by reference, discloses a colorant for natural or synthetic resinous or polymeric materials, having the formula:

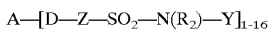

A—[D—Z—SO$_2$—N(R$_2$)—Y]$_{1-16}$ wherein R$_2$ is selected from hydrogen, methyl, cyclohexyl, phenyl, or Y; A is a nonionic metallophthalocyanine chromophore which can be substituted for example with halogen, alkyl, alkoxy, alkylthio, or aryloxy; Z is an arylene moiety; D is a linking group being or containing at least one of —O—, —S—, —SO$_2$—, —N(R$_3$)—, or —N(SO$_2$R$_4$)— as the linking moiety, wherein R$_4$ is unsubstituted or substituted alkyl, cycloalkyl, or aryl, and R$_3$ is R$_4$ or hydrogen; Y is a poly(oxyalkylene) moiety containing at least three monomeric units of the formula (—RO—) wherein each R is straight or branched alkylene of 1–4 carbons or mixtures thereof, up to about 20 mole percent of said monomeric units may be connected by one or more linking groups such as alkyleneoxy, —NH—, or —NHCONH—, and wherein Y can be terminated by hydrogen, or by or contain as branch substituents, 1–3 groups or moieties selected from alkyl, cycloalkyl, acyl, or aryl; wherein any of the above recited hydrocarbon groups, moieties or substituents may themselves be substituted with up to four substituents selected, for example, from alkyl, halogen, mercapto, alkoxycarbonyl, hydroxy, alkoxy, or the like; and wherein each aliphatic hydrocarbon portion or moiety of the groups, moieties or substituents recited above contains from 1–20 carbons.

U.S. Pat. No. 4,875,903 (Pedrazzi), the disclosure of which is totally incorporated herein by reference, discloses compounds of the formula

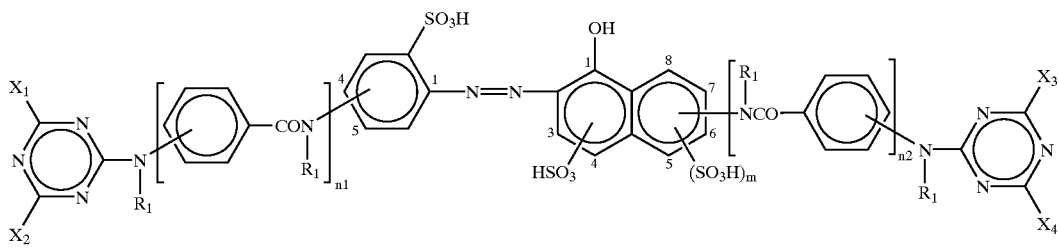

wherein each R$_1$ is independently hydrogen, C$_{1-4}$ alkyl, or C$_{1-4}$ alkyl monosubstituted by hydroxy, halo, cyano, or C$_{1-4}$ alkoxy, each of X$_1$ and X$_3$ is independently halo, hydroxy, C$_{1-4}$ alkyl, C$_{1-4}$ alkoxy, phenyl, phenoxy, amino, or an aliphatic, cycloaliphatic, aromatic, or heterocyclic amino group, each of X$_2$ and X$_4$ is independently an aliphatic, cycloaliphatic, aromatic, or heterocyclic amino group containing at least one protonatable nitrogen atom or quaternary ammonium group, m is 0 or 1, and each of n$_1$ and n$_2$ is independently 0 or 1, with the proviso that n$_1$+n$_2$ is 1 or 2, wherein each halo is independently fluoro, chloro, or bromo, with the provisos that (1) the total number of basic and cationic groups present as X$_1$–X$_4$ equals or exceeds the number of sulfo groups, (2) the hydroxy or alkoxy group of each hydroxy- or alkoxy-substituted alkyl group or alkylene radical attached to a nitrogen atom is bound to a carbon atom other than the C$_1$-atom, and (3) the hydroxy groups of each alkylene radical substituted by two hydroxy groups are attached to different carbon atoms, mixtures of such compounds, and salts and mixtures with one or more copper phthalocyanine dyes containing basic and/or cationic groups. The materials are suitable for dyeing or printing hydroxy group- or nitrogen-containing organic substrates as such or in form of solid or liquid aqueous dye preparations. They are also suitable for dyeing glass and products thereof and the preparation of inks.

U.S. Pat. No. 3,674,494 (Hoffmann et al.), the disclosure of which is totally incorporated herein by reference, discloses improved relief plates, particularly printing plates, prepared by exposing under an image-bearing transparency a layer, which can be crosslinked by exposure and has been applied to a light-reflecting substrate of a substantially homogeneous mixture of solid polymers, monomers, photoinitiators, and, if desired, polymerization inhibitors, which mixture also contains finely dispersed therein a soluble metal complex dye, and washing out the unexposed areas.

PCT Patent Application WO 98/14520 (Wolleb), the disclosure of which is totally incorporated herein by reference, discloses a phthalocyanine or its metal complex of a divalent metal, oxometal, halogenometal, or hydroxymetal, which comprises at least one unsubstituted or substituted formyl, carbonyl, hydroxymethyl, or carboxyl group which is attached at the peripheral carbon skeleton. These phthalocyanines or their derivatives are used in recording layers of optical recording media. There is also claimed a novel process for the preparation of some of these compounds corresponding to the formula

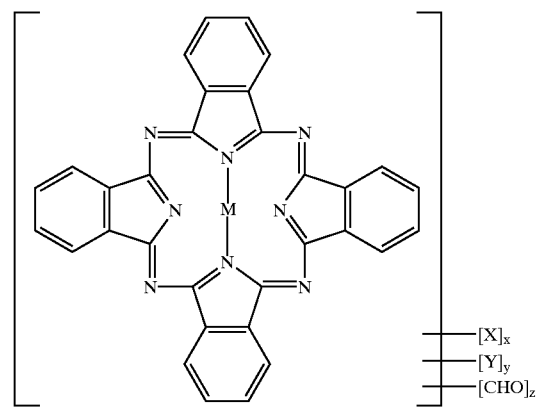

wherein M is a divalent metal, oxometal, halogenometal, or hydroxymetal, or two hydrogen atoms, X is halogen, or 2X in vicinal position on a phenyl ring form together a —C=C—C=C— bridge so that an additional phenyl ring is obtained, Y is —OR$_1$, —OOCR$_2$, —NHR$_1$, —N(R$_1$)R$_2$, or —SR$_1$, x is 0 or a number from 1 to 8, y depending on z is a number from z to 4, and z is a number from 1 to 4, by reacting a compound of the formula

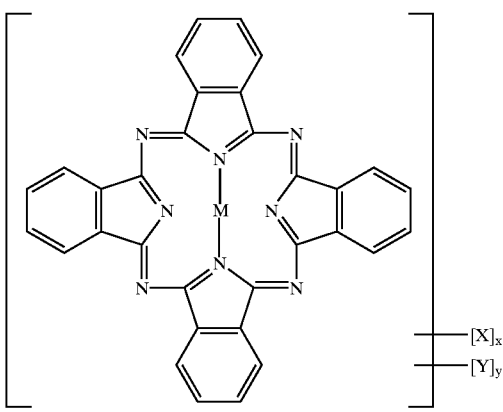

wherein M, X, Y, x, and y are as defined above, with z moles each of dimethylformamide and phosphoryl chloride.

European Patent Application EP 0742255 (Wolleb et al.), the disclosure of which is totally incorporated herein by reference, discloses the coloration of high molecular weight organic materials in the mass with soluble phthalocyanine precursors of structure

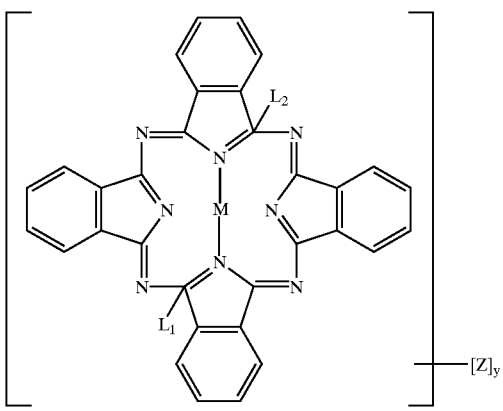

or isomers thereof, to the soluble phthalocyanine precursors as such wherein M is Zn, Ti, or V or wherein $L_1$ is morpholino, pyrrolidino or $C_1$–$C_{12}$ alkyl substituted piperidino, to compositions containing high molecular weight organic materials and the above soluble phthalocyanine precursors, and to a process for making structured color images and applications thereof.

European Patent Application EP 787732 (Reynolds et al.), the disclosure of which is totally incorporated herein by reference, discloses phthalocyanine compounds substituted by from 1 to 8 substituents of formula (—O—R—O—) wherein R is a 1,2-arylene group. Preferably, the phthalocyanine compounds are substituted by catechol. Additional substituents which may be present include hydrocarbyloxy, hydrocarbylthio, halogen, and sulfonic acid or a salt thereof.

European Patent Publication EP 1013721 (Stawitz), the disclosure of which is totally incorporated herein by reference, discloses solid preparations of metal-containing or metal-free phthalocyanine dyes which have an average particle size of greater than 100 microns and which have a pH of greater than or equal to 10 when dissolved in 10 times the amount of water. The dyes are particularly suitable for the dyeing and printing of paper, after dissolution in water.

European Patent Publication EP 540953 (Gerson et al.), the disclosure of which is totally incorporated herein by reference, discloses solid solutions containing (a) about 90 to about 10 percent by weight of a chlorinated copper phthalocyanine containing about 14 to about 16 atoms of chlorine per molecule, and (b) about 10 to about 90 percent by weight of a copper phthalocyanine containing about 3 to about 4 atoms of chlorine, wherein said compositions are characterized by X-ray diffraction patterns that differ from the sum of the X-ray diffraction patterns of the individual components.

European Patent Publication EP 714954 (Moeckli et al.), the disclosure of which is totally incorporated herein by reference, discloses cationic imidazole azo dyes of the formulae (1) (2) and (3)

in which A and $A_1$ independently of one another are each a radical of the formula (4)

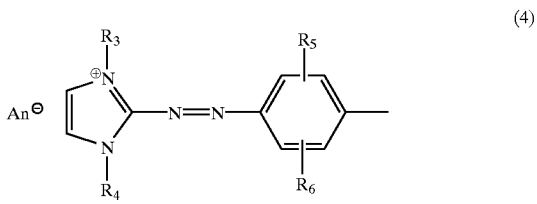

Z is the radical of an aliphatic or aromatic diamine, $R_1$ and $R_2$ are each hydrogen or substituted or unsubstituted $C_1$–$C_4$ alkyl or, together with the two nitrogen atoms to which they are attached and with Z, form a 5-, 6-or 7-membered ring, X is the radical of a bridging member, n is 2, 3 or 4, $Z_1$ is the radical of an aromatic diamine, $Z_2$ is the radical of an aliphatic diamine, KK is the radical of a coupling component, $R_3$ and $R_4$ are each hydrogen or substituted or unsubstituted $C_1$–$C_4$ alkyl, $R_5$ and $R_6$ independently of one another are each hydrogen or substituted or unsubstituted $C_1$–$C_4$ alkyl or $C_1$–$C_4$ alkoxy, and An⁻ is a colorless anion, are particularly suitable for the dyeing of paper in red or violet shades having good fastness properties.

European Patent Publication EP398716 (Tsuchida et al.), the disclosure of which is totally incorporated herein by reference, discloses a pigment composition capable of giving a pigment dispersion which has excellent fluidity, high gloss, and high coloring power and is free from bluish tint, which comprises 100 parts by weight of at least one highly halogenated copper phthalocyanine and 0.3 to 30 parts by weight of a highly halogenated aluminum phthalocyanine.

European Patent Publication EP 209487 (Langley et al.), the disclosure of which is totally incorporated herein by reference, discloses pigmentary copper phthalocyanine prepared by converting crude copper phthalocyanine by methods known per se in the presence of trichlorophenoxy copper phthalocyanine. The resulting pigment is heat resistant and solvent resistant.

Japanese Patent Publication JP 8302224 (Toshihiro et al.), the disclosure of which is totally incorporated herein by reference, discloses a compound of formula I

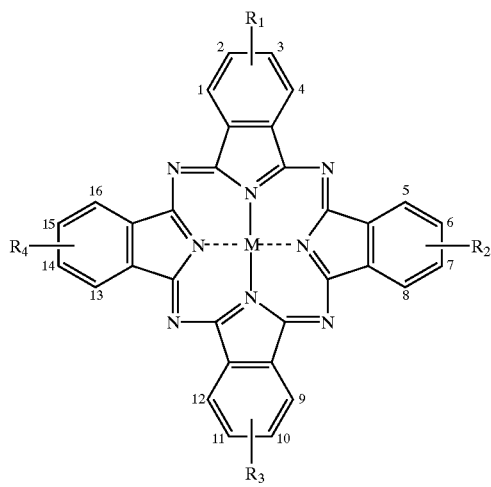

wherein $R_1$ to $R_4$ are each formula 11

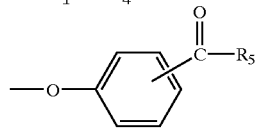

[$R_5$ is an alkyl, an alkoxy, a (substituted) phenyl(oxy) or a benzyl(oxy)]; regarding the positions of $R_1$ to $R_4$, $R_1$ is at $C_1$ or $C_4$, $R_2$ is at $C_5$ or $C_8$, $R_3$ is at $C_9$ or $C_{12}$, and $R_4$ is at $C_{13}$ or $C_{16}$; M is a pair of H atoms, a divalent metal, or a metal derivative of a trivalent or tetravalent metal. Further, the compound is preferably obtained by reacting (A) a phthalonitrile compound of formula III

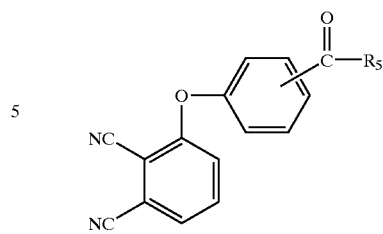

with (B) a metal derivative (e.g. palladium chloride) e.g. in a ratio of the component B: the component A of 1:3 to 1:6 (mol ratio) in the presence of a catalyst such as 1,8-diazabicyclo[5,4,0]-7-undecene in a solvent such as n-aminoalcohol at 130–230° C. for 5 to 15 hours. The compound has a high solubility and absorption coefficient and is capable of providing a color filter excellent in transparency behavior, light resistance, and heat resistance.

Japanese Patent Publication JP 8225751 (Masaji et al.), the disclosure of which is totally incorporated herein by reference, discloses a compound obtained by reacting (A) a phthalonitrile compound of formula I

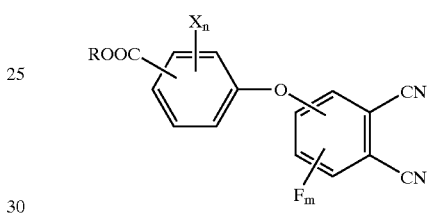

(COOR is a carboxylic acid ester having a heterocycle; X is a halogen, etc.; m is an integer of 0–3; n is an integer of 0–4) with (B) a metallic compound and expressed by (C) the formula II

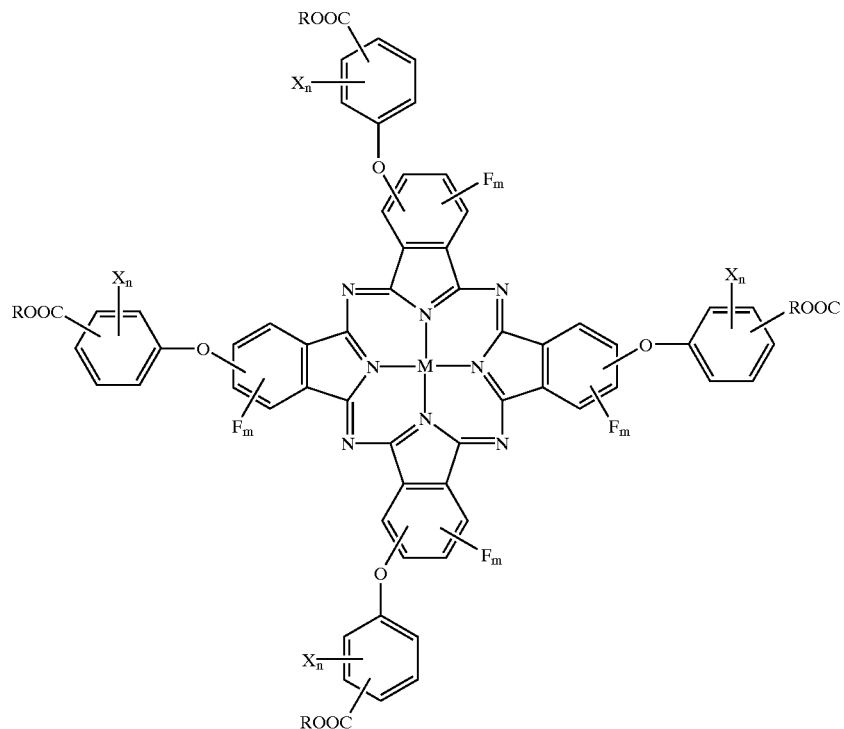

in which 1–8 pieces of benzene nuclei in 16 substitutable positions in a phthalocyanine skeleton are substituted with phenoxy and the phenoxy is substituted with a carboxylic acid ester having more than one heterocycles (M is a metal, a metal oxide or a metal halide). The objective optical recording medium is obtained by adding the compound to a recording medium placed on a substrate. The compound has excellent absorbing properties, solubility, light resistance, and economical efficiency and is useful for a near-infrared absorbing pigment, especially for an addition-type optical recording medium.

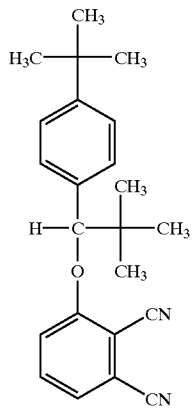

Japanese Patent Publication JP 9279050 (Shuichi et al.), the disclosure of which is totally incorporated herein by reference, discloses a phthalocyanine compound prepared by a process in which equimolar amounts of a phthalonitrile compound (e.g. 3-[4-t-butyl-α-iso-propylbenzyloxy] phthalonitrile) represented by formula I and an organic base (e.g. 1,8-diazabicyclo[5.4.0]-7-undecene) are dissolved in a solvent (e.g. amyl alcohol) under heating. A metal compound (e.g. $CuCl_2$) is added to the solution under agitation, and heated, and the solvent is removed from the reaction mixture in a vacuum after the reaction to obtain a phthalocyanine compound (e.g. compound represented by formula II)

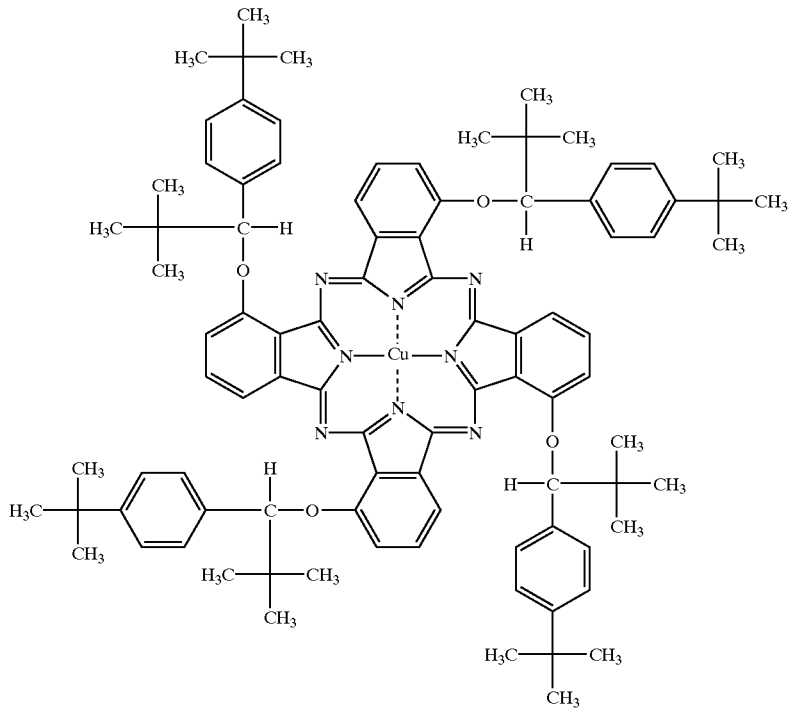

containing several isomers represented by formula III

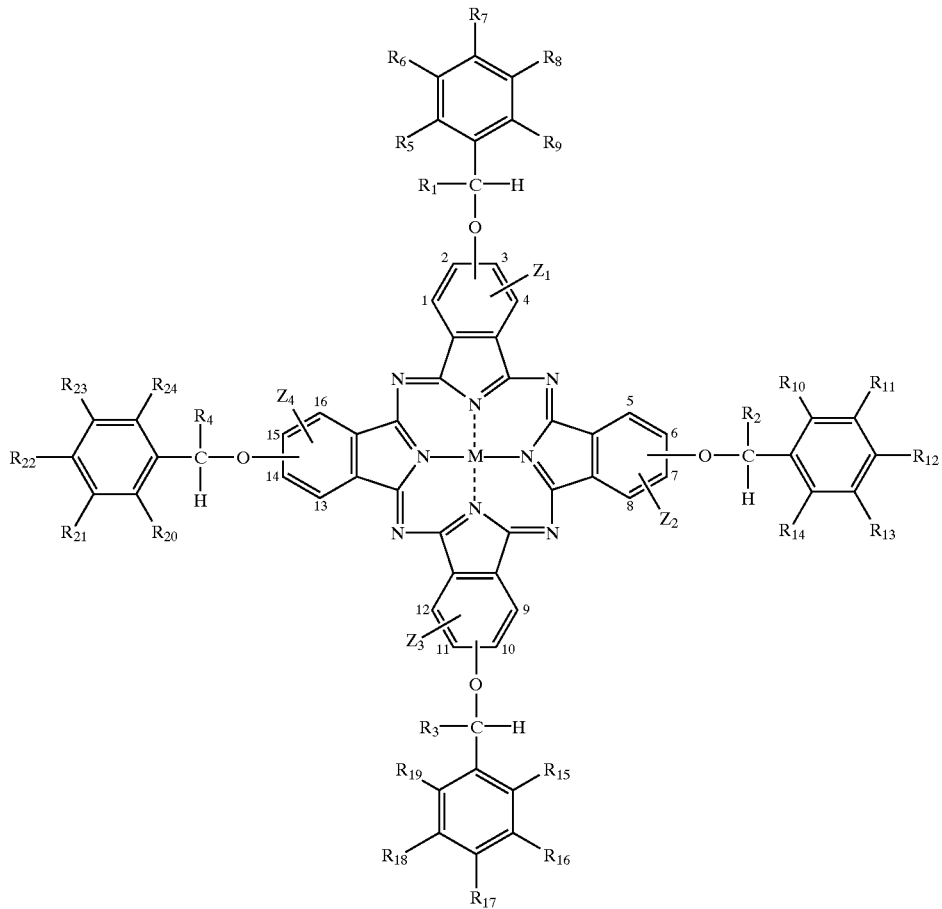

(wherein $R_1$ to $R_4$ are each a 1–6 C alkyl; $R_5$ to $R_{24}$ are each H, a halogen, a 1–6 C alkyl, a 1–6 C fluoroalkyl or the like; $Z_1$, to $Z_4$ are each H or a halogen; and M is a divalent metal atom, a tri- or tetra-valent substituted metal atom or the like). Next, a film of a mixture of the phthalocyanine compound with a binder is formed on a base made of, e.g. an acrylic resin by, e.g. spin coating to obtain a recording layer having a thickness of about 100 angstroms to 5 microns.

Japanese Patent Publication JP 5086301 (Naoto et al.), the disclosure of which is totally incorporated herein by reference, discloses compounds of formulas I to IV

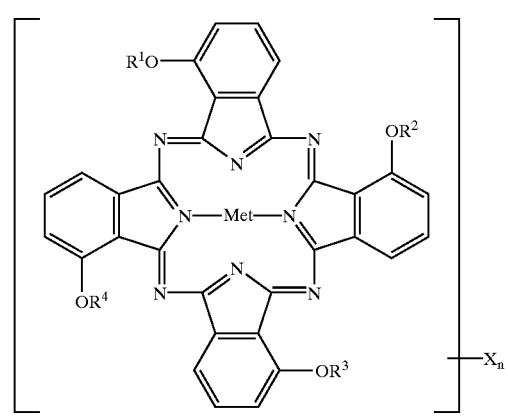

(1)

-continued

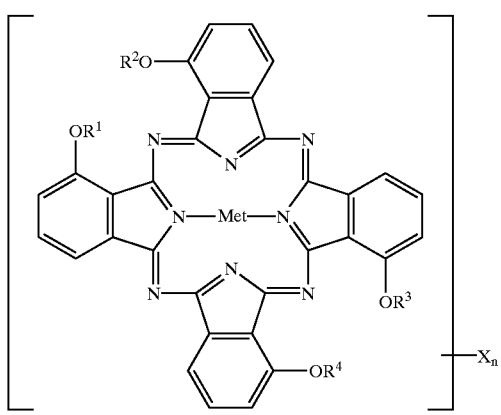

(2)

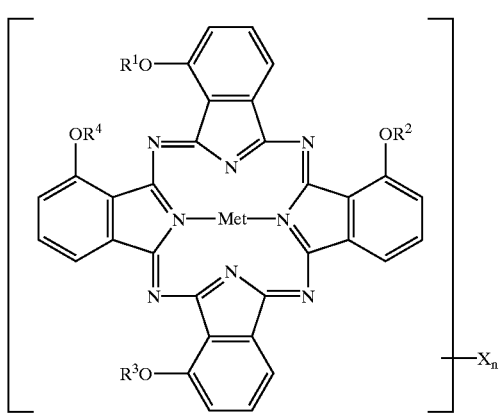

(3)

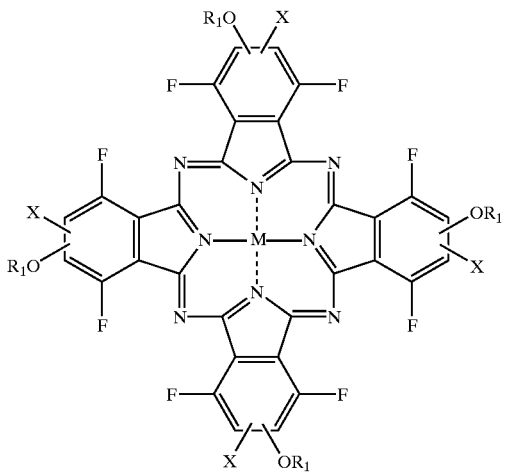

wherein X is F, $OR_2$, or $SR_4$, $R_1$, $R_2$, and $R_3$ are each a 1 to 20 carbon alkyl group, a 4 to 6 carbon cycloalkyl group, or a phenyl, benzyl, or naphthyl group optionally substituted by halogen or by a 1 to 4 carbon alkyl or 1 to 4 carbon alkoxyl group, and M is a metal, a metal oxide, or a metal halide. The compound is produced by reacting a phthalonitrile compound of the formula

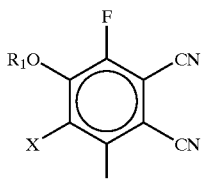

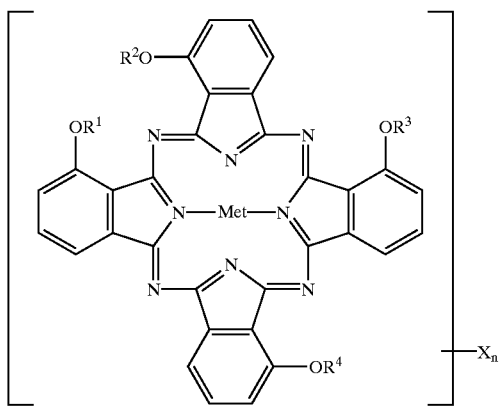

(4)

with a metal oxide or halide or a metal salt of an organic acid of the formula $M_m X_n$ wherein M is a metal or a metal oxide, X is O, halogen, or an organic acid group, and m and n are each 1 to 5. The phthalocyanine compound has an absorption band in the near-infrared region of 650 to 900 nanometers and an excellent solubility especially in an alcoholic solvent.

Japanese Patent Publication JP 62111249 (Norihito et al.), the disclosure of which is totally incorporated herein by reference, discloses a photosensitive composition principally comprising a photosensitive diazo resin and a lipophilic high molecular compound, wherein said photosensitive composition further contains a metal complex dye soluble in an organic solvent. Also disclosed is a photosensitive lithographic printing plate employing such a photosensitive composition.

Japanese Patent Publication JP 61146597 (Michitoku et al.), the disclosure of which is totally incorporated herein by reference, discloses a way to obtain a clear half-tone transfer picture of higher density levels than in the case of transfer using only dye by a method in which a thermal transfer ink sheet is made up using a filler and a dye so as to obtain the same hue and the recording density in the high-density region is complemented by the transfer of the filler. A toluene solution of polyester resin is coated on a base material of condenser paper and dried to form an intermediate adhesive layer. A solution of Kayaset blue-K-FL as a dye, an aliphatic amide as a low-melting substance, a paraffin wax as an auxiliary to lower the viscosity of the low-melting substance, and copper phthalocyanine as inorganic pigment filler in acetone is coated by a bar coater on wherein $R^1$ to $R^4$ are each a 6 to 9 carbon alkyl group having 2 to 4 secondary, tertiary, or quaternary carbon atoms, Met is a divalent metal atom, a monosubstituted trivalent metal atom, or a disubstituted tetravalent metal atom, X is halogen, and n is 1 to 4. The compound is excellent in solubility in a solvent and useful as a compound for forming a recording layer of an optical recording medium which has high refractive index and sensitivity.

Japanese Patent Publication JP 5222302 (Koji et al.), the disclosure of which is totally incorporated herein by reference, discloses a phthalocyanine compound of the formula the intermediate layer and dried to form an ink layer. A recording paper is laminated on the ink layer side of the ink sheet and solid transfer printing is made by using a thermal facsimile device to obtain clear cyanine-color transfer picture.

Japanese Patent Publication JP 58196295 (Makoto), the disclosure of which is totally incorporated herein by reference, discloses a way to recognize easily the surface part of a metal plate covered with a solid lubricant with the eye and to prevent the deterioration of pressing properties and dragging resistance caused by unevenness of coating, by adding a colorant to a solution of the solid lubricant. A solid lubricant consisting essentially of metallic soap, higher fatty acid, wax, etc. or a solid lubricant consisting essentially of an organic synthetic resin such as water-soluble acrylic polymer, etc. is blended with pigment or dye such as copper phthalocyanine blue, etc. in a volume ratio of usually (25:1)–(50:1).

Japanese Patent Publication JP 00290577 (Naoaki et al.), the disclosure of which is totally incorporated herein by reference, discloses a way to improve pigment-dispersing properties and resistance to drying by compounding a pigment, water, a water-soluble organic solvent and caprolactam. With a mixed solvent comprising water and 2 to 60 weight percent, preferably 5 to 35 weight percent, of a water-soluble organic solvent are admixed 1 to 25 weight percent, preferably 2 to 15 weight percent, of an inorganic pigment such as carbon black, ultramarine blue, or the like or an organic pigment such as copper phthalocyanine blue, benzidine yellow, or the like, 0.1 to 20 weight percent, preferably 1 to 10 weight percent of caprolactam of the formula and, as required, additives such as a pH adjusting agent, an antiseptic agent, a mildew-proofing agent, a fluorine-containing surfactant, a nonionic, anionic or cationic surfactant, an anti-foaming agent or the like. This ink composition hardly suffers from flocculation and sedimentation of pigments and can maintain not only the same density of handwriting as in the initial stage even when filled in a writing tool and left upright or upside-down but also the same volume of an ink discharged in writing as in the initial stage even when a writing tip is left exposed to the outside and the solid content is raised by evaporation of a solvent. "Synthesis and Characterization of Di-disubstituted Phthalocyanines," J. G. Young and W. Onyebuagu, *J. Org. Chem.*, Vol. 55, No. 7, p. 2155 (1990), the disclosure of which is totally incorporated herein by reference, discloses an improved approach to the synthesis of di-disubstituted phthalocyanines from two different phthalyl precursors. The method combines substituted 1,3-diiminoisoindoles and 6/7-nitro-1,3,3-trichloroisoindolenine to synthesize phthalocyanine. The method can be applied to the synthesis of hydrogen and metallo phthalocyanine. The yields are variable, ranging from 17 percent to 72 percent depending on the substituents. "Separation of 2(3),9(10),16(17),23(24)-Tetrasubstituted Phthalocyanines with Newly Developed HPLC Phases," M. Sommerauer, C. Rager, and M. Hanack, *J. Am. Chem. Soc.*, Vol. 118, No. 42, p. 10085 (1996), the disclosure of which is totally incorporated herein by reference, discloses the synthesis of 2(3),9(10),16(17),23(24)-tetrasubstituted phthalocyanines from 1,2-dicyano-4-alkoxybenzenes or the corresponding isoindolines. In each case, four isomers with $D_{2h}$, $C_{4h}$, $C_{2v}$, and $C_s$ symmetry were obtained in the statistical expected yield. The separation of the $C_{4h}$ and the $D_{2h}$ isomers was achieved successfully for the first time from the other two isomers with newly developed HPLC phases based on π-π interactions. In one case, a particular phthalocyanine could be separated into four different isomers and characterized by UV/vis and $^1$H-NMR spectroscopy. Because of line broadening at room temperature, $T_1$ and $T_2$ relaxation time measurements of two phthalocyanines at different temperatures were carried out. Whether the broad peaks are attributable to aggregation or attributable to a short relaxation time is explained.

"The Synthesis of Pure 1,11,15,25-tetrasubstituted Phthalocyanines as Single Isomers Using Bisphthalonitriles," D. M. Drew and C. C. Leznoff, *Synlett*, 1994 (Ang), p. 623, the disclosure of which is totally incorporated herein by reference, discloses bisphthalonitriles linked by 2,2-disubstituted propan-1,3-diol precursors which gave pure 1,11,15,25-substituted isomers of mononuclear phthalocyanine derivatives upon homocyclization. Reasonable yields of these phthalocyanines could be obtained with limited polymeric side-products utilizing modified cyclization methods. The $^1$H NMR spectrum of these phthalocyanines exhibited the discrete doublet-triplet-doublet proton signals expected of a pure isomer.

*Phthalocyanines: Properties and Applications*, C. C. Leznoff and A. B. P. Lever, eds., the disclosure of which is totally incorporated herein by reference, discloses at p. 35 various substituted phthalocyanines.

"Synthesis of Novel Unsymmetrically Substituted Push-Pull Phthalocyanines," A. Sastre, B. del Rey, and T. Torres, *J. Org. Chem.*, Vol. 61, No. 24, p. 8591 (1996), the disclosure of which is totally incorporated herein by reference, discloses the synthesis and characterization of novel noncentrosymmetrically push-pull substituted metal-free phthalocyanines. The compounds had different donor (dialkoxy, tert-butyl, methyl, p-tolylthio) and/or attractor (p-tolylsulfinyl, p-tolylsulfonyl, nitro) functional groups, were soluble in organic solvents, and were especially designed to study their second- and third-order nonlinear optical properties. For preparing the unsymmetrical phthalocyanines, the effectiveness of the subphthalocyanine route, using different substituted diiminoisoindolines as reagents, was tested. A comparison between this method versus the statistical one was done. The results obtained showed that the ring enlargement reaction of subphthalocyanines to obtain unsymmetrically substituted phthalocyanines is not a selective reaction but a multistep process, which depends dramatically on the nature of the substituents on the subphthalocyanines, the reactivity of the iminoisoindoline, the solvent, and other factors that limit its general synthetic utility. Preliminary data of the experimental second-order hyperpolarizabilities of some compounds were also given.

Although the phthalocyanines discussed above are considered to be soluble in organic media, they are not necessarily suited for use as phase change ink colorants. Accordingly, while known compositions and processes are suitable for their intended purposes, a need remains for improved colorant compositions. In addition, a need remains for improved phthalocyanine compositions. Further, a need remains for colorants suitable for use in phase change inks. Additionally, a need remains for colorants that enable good to excellent lightfastness. There is also a need for improved colorants having improved cyan color for primary subtractive imaging. In addition, there is a need for improved colorants having high tinctorial power or spectral strength. Further, there is a need for improved cyan phase change ink colorants that are highly thermally stable in ink compositions for several weeks in air at temperatures exceeding 140° C. Additionally, there is a need for phase change ink colorants with low diffusion characteristic that will not bleed into inks containing other colorants. A need also remains for colorants with good to excellent lightfastness that are compatible with phase change ink vehicles. In addition, a need remains for colorants suitable for use in phase change inks that exhibit reduced or no variation in color over the life of the ink in the printer. Further, a need remains for colorants suitable for use in phase change inks that exhibit reduced or no variation in color subsequent to being deposited in imagewise fashion on substrates. Additionally, a need remains for colorants that have no carcinogenic or mutagenic effects. There is also a need for colorants that, when dissolved in phase change ink carriers, do not leave residues of material that might otherwise complicate filtration efficiency. There is also a need for phase change inks of good lightfastness that perform well when substrates imaged with the inks are passed through automatic document feed subsystems in copiers and printers. In addition, there is a need for phase change inks that exhibit reliable jetting characteristics and good long term performance in ink jet printers. Additionally, there is a need for preparative processes for phase change ink colorants that use low cost starting materials. A need also remains for preparative processes for colorants that use starting materials that are readily commercially available in large quantities. In addition, a need remains for preparative processes that use low cost, readily available solvents. Further, a need remains for preparative processes that do not generate hazardous waste that requires special handling and disposal procedures. Additionally, a need remains for methods for preparing colorants with the above advantages that enables preparation of a colorant product with reduced or no solubility problems in phase change ink vehicles as a result of incomplete reactions in the synthetic process. There is also a need for methods for preparing colorants with the above advantages that enables preparation of a colorant product without the need to handle unstable intermediate products with limited shelf life. In addition, there is a need for methods for preparing colorants with the above advantages that enables preparation of a colorant product without the need for severe reaction conditions. Further, there is a need for methods for preparing colorants with the above advantages that enables preparation of a colorant product without the need for elaborate purification procedures, such as column chromatography or the like. Additionally, there is a need for methods for preparing colorants with the above advantages that enables preparation of a colorant product without the need to carry out dangerous derivatization procedures. A need also remains for methods for preparing colorants with the above advantages that enables preparation of a colorant product in high yield. In addition, a need remains for methods for preparing colorants with the above advantages that enables preparation of a colorant product in high purity. Further, a need remains for methods for preparing colorants with the above advantages that enables preparation of a colorant product with reduced costs associated with the synthesis. Additionally, a need remains for methods for preparing colorants with the above advantages that enables colorant synthesis with a high degree of reliability.

SUMMARY OF THE INVENTION

The present invention is directed to a process for preparing a colorant of the formula

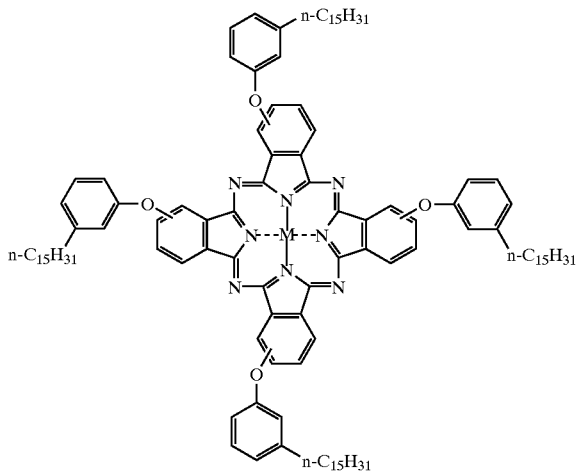

wherein M is an atom or group of atoms capable of bonding to the central cavity of a phthalocyanine molecule, wherein axial ligands optionally can be attached to M, which comprises (a) reacting 3-n-pentadecylphenol with 4-nitrophthalonitrile in the presence of a base to form an alkylarylether adduct of phthalonitrile; and (b) reacting the alkylarylether adduct of phthalonitrile with either (i) a metal compound, or (ii) an ammonia-releasing compound in the presence of an alkanolamine solvent, or (iii) mixtures of (i) and (ii), to form the colorant.

DETAILED DESCRIPTION OF THE INVENTION

The present invention is directed to methods of making compounds of the formula

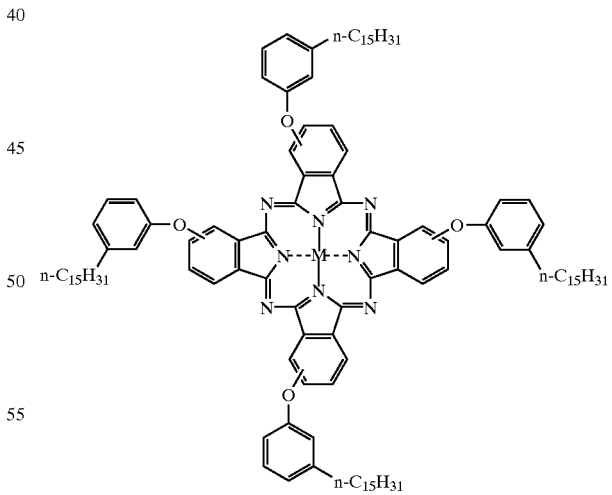

wherein M is an atom or group of atoms capable of bonding to the central cavity of a phthalocyanine molecule, wherein axial ligands optionally can be attached to M. About seventy atoms or groups are known to bond in the central cavity of a phthalocyanine molecule, as disclosed in, for example, Phthalocyanine Materials, N. B. McKeown, Cambridge University Press (1998), Chapter 1, Table 1.1, the disclosure of which is totally incorporated herein by reference, including, but not limited to, two hydrogen, lithium, sodium, or potassium atoms; a divalent metal atom, such as beryllium, magnesium, calcium, strontium, barium, chromium, manganese, iron, cobalt, nickel, copper, zinc, tin, lead, cadmium, and the like; a divalent halometal or -metalloid group, such as chloroiron(III), chlorotitanium (III), chlorochromium(III), chloroaluminum, chlorogallium, chloroindium, chlorophosphorus(III), dichlorotitanium(IV), dichlorosilicon, dichlorogermanium, dichlorotin, and the like, as well as the corresponding fluorides, bromides, and iodides; a divalent hydroxy metal group, such as hydroxyaluminum, hydroxygallium, dihydroxysilicon, dihydroxygermanium, dihydroxytin, and the like; a divalent oxo-metal group, such as oxo-molybdenum(IV), oxo-vanadium(IV), oxo-titanium(IV), and the like; a divalent metal- or metalloidal-oxyhydrocarbon group, such as alkoxyaluminum, alkoxygallium, dialkoxysilicon, diaryloxygermanium, and the like, wherein the oxyhydrocarbon group is an oxyalkyl group, an oxyaryl group, an oxyalkylaryl group, an oxyarylalkyl group, an oxyheterocyclic group, or mixtures thereof, and typically (although not necessarily) contains from one to about twenty carbon atoms; and the like, as well as mixtures thereof.

It is believed that in most instances the colorant molecules of the present invention are obtained as mixtures of four isomeric forms as illustrated below, wherein the $C_{4h}$, $D_{2h}$, $C_{2v}$, and $C_s$, isomers are present in the approximate ratio of, respectively, about 1:1:2:4:

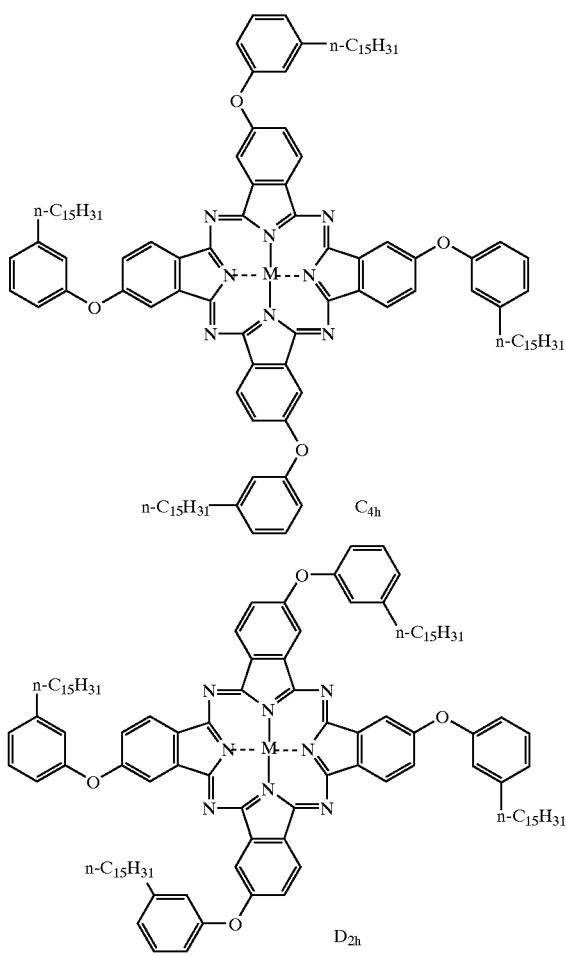

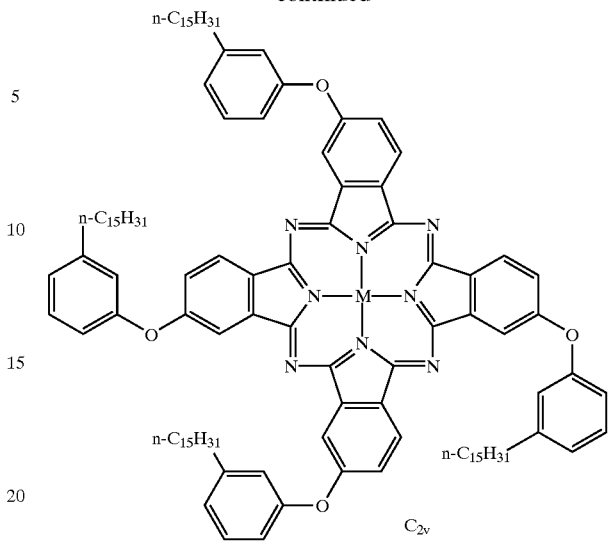

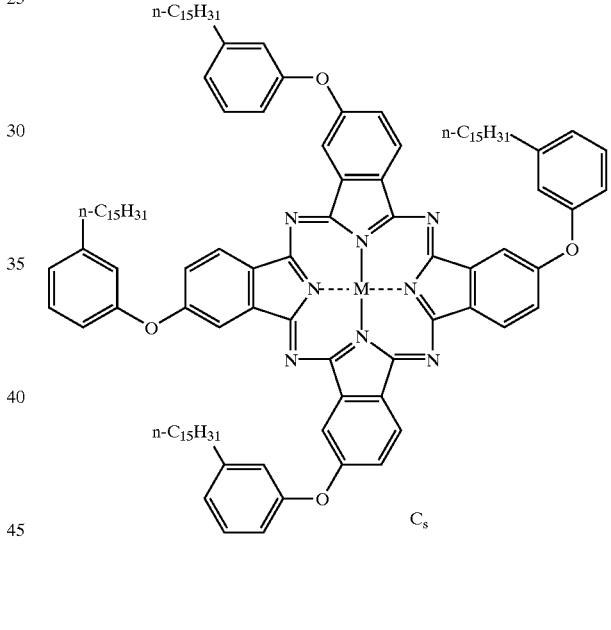

In one embodiment, the colorant molecules of the present invention exhibit a spectral strength, measured as described prior to the Examples hereinbelow, in one embodiment of at least about $1 \times 10^5$ milliliters absorbance per gram, and in another embodiment of at least about $1.15 \times 10^5$ milliliters absorbance per gram, and in one embodiment of no more than about $1.5 \times 10^5$ milliliters absorbance per gram, and in another embodiment of no more than about $1.3 \times 10^5$ milliliters absorbance per gram, although the spectral strength can be outside of these ranges.

The colorant molecules of the present invention are prepared in two steps, the first of which is the synthesis of the alkylarylether adduct of phthalonitrile (4-(3-n-pentadecyl) phenoxyphthalonitrile):

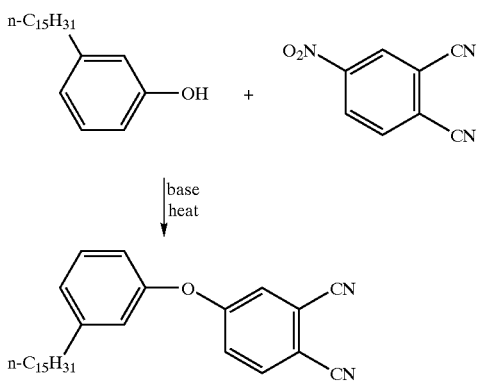

This process can be carried out by reacting the desired $C_{15}$ phenol (3-n-pentadecylphenol) with 4-nitrophthalonitrile in the presence of a base. Examples of suitable $C_{15}$ phenols are commercially available as, for example, CARDOLITE®, predominantly a meta $C_{15}$ alkyl phenol obtained from cashew nut distillation and containing small amounts of naturally occurring isomers thereof, available from Cardolite Corporation, Newark, N.J., and AF 6518, available from Palmer International Inc., Worchester Pa., also predominantly a meta $C_{15}$ alkyl phenol obtained from cashew nut distillation and containing small amounts of naturally occurring isomers thereof. Suitable bases include both organic and inorganic bases. Examples of organic bases include (but are not limited to) trialkyl amines (including triethylamine, tripropylamine, tributylamine, and the like), piperidine, 1,4-diazabicyclo[2.2.2]octane, and the like, as well as mixtures thereof. Examples of inorganic bases include (but are not limited to) lithium hydroxide, sodium hydroxide, potassium hydroxide, lithium carbonate, sodium carbonate, potassium carbonate, lithium hydride, sodium hydride, potassium hydride, lithium alkoxide, sodium alkoxide, potassium alkoxide (wherein the alkoxide can be, but is not limited to, methoxide, ethoxide, propoxide, butoxide (including t-butoxide), and the like), and the like, as well as mixtures thereof. The reactants are dissolved in any solvent capable of dissolving the reactants, such as methanol, ethanol, propanol, butanol, dioxane, acetone, toluene, nitrobenzene, dimethyl formamide, dimethyl sulfoxide, 1-methyl-2-pyrrolidinone, 1-cyclohexyl-2-pyrrolidinone, sulfolane, and the like, as well as mixtures thereof. The solids content of the reaction mixture in one embodiment is at least about 0.5 parts by weight solvent per every 1 part by weight $C_{15}$ phenol, and in another embodiment is at least about 2 parts by weight solvent per every 1 part by weight $C_{15}$ phenol, and in one embodiment is no more than about 20 parts by weight solvent per every 1 part by weight $C_{15}$ phenol, and in another embodiment is no more than about 6 parts by weight solvent per every 1 part by weight $C_{15}$ phenol, although the solids content can be outside of these ranges. Typically, the $C_{15}$ phenol and the base are added to the solvent, followed by heating the reaction mixture, in one embodiment to a temperature of at least about 30° C., and in another embodiment to a temperature of at least about 80° C., and in one embodiment to a temperature of no more than about 150° C., and in another embodiment to a temperature of no more than about 120° C., although the temperature can be outside of these ranges, for a period of time in one embodiment of at least about 0.25 hour, and in another embodiment of at least about 0.5 hour, and in one embodiment of no more than about 8 hours, and in another embodiment of no more than about 2 hours, although the time can be outside of these ranges. By allowing the $C_{15}$ phenol and the base to react first, the $C_{15}$ phenoxide salt is formed; optionally, the 4-nitrophthalonitrile can be added with the $C_{15}$ phenol and the base in a single step, in which case the preheating step is eliminated. Thereafter, the 4-nitrophthalonitrile is added to the reaction mixture and the reaction mixture is then heated, in one embodiment to a temperature of at least about 30° C., and in another embodiment to a temperature of at least about 70° C., and in one embodiment to a temperature of no more than about 150° C., and in another embodiment to a temperature of no more than about 110° C., although the temperature can be outside of these ranges, for a period of time in one embodiment of at least about 0.25 hour, and in another embodiment of at least about 0.5 hour, and in one embodiment of no more than about 24 hours, and in another embodiment of no more than about 4 hours, although the time can be outside of these ranges. Thereafter, the reaction mixture is cooled, in one embodiment to a temperature of at least about 20° C., and in one embodiment to a temperature of no more than about 100° C., and in another embodiment to a temperature of no more than about 60° C., although the temperature can be outside of these ranges, followed by quenching in a precipitant solvent, such as water, methanol, mixtures thereof, and the like, by stirring the reaction solution into the precipitant solvent or vice-versa, in an amount in one embodiment of at least about 0.25 part by weight precipitant solvent per every 1 part by weight reaction solution, and in another embodiment of at least about 0.5 part by weight precipitant solvent per every 1 part by weight reaction solution, and in one embodiment of no more than about 2 parts by weight precipitant solvent per every 1 part by weight reaction solution, and in another embodiment of no more than about 10 parts by weight precipitant solvent per every 1 part by weight reaction solution, although the relative amounts can be outside of these ranges, thereby causing precipitation of the alkylaryloxyphthalonitrile intermediate product, which can be isolated by filtration. Thereafter, the intermediate can be reslurried with water or dilute acid (for example, 2 percent wt/volume hydrochloric acid) or base (for example, 2 percent sodium hydroxide) and filtered, and then reslurried and filtered with pure water, and the process repeated until inorganic and/or organic salts are removed from the product and the filtrate is of neutral pH and has a conductivity of less than about 20 microSiemens. If desired, the product can be further purified by slurrying it in a solvent, such as methanol, ethanol, propanol, isopropanol, acetone, N,N'-dimethylformamide, mixtures thereof, mixtures of one or more of these solvents with water, and the like, followed by isolation of the product by filtration, which process may remove minor organic contaminants from the alkylaryloxyphthalonitrile intermediate. Thereafter, the solid product can, if desired, be dried by heating under vacuum at a temperature in one embodiment of at least about 20° C., and in another embodiment of at least about 25° C., and in one embodiment of no more than about 100° C., and in one embodiment of no more than about 50° C., although the temperature can be outside of these ranges, for a period in one embodiment of at least about 1 hour, and in one embodiment of no more than about 72 hours, although the time can be outside of these ranges. The yield of the dried product typically (although not necessarily) ranges from about 80 to 90 percent. Purity of the final product in one embodiment (although not necessarily) is greater than about 98 percent, as ascertained by any conventional analytical technique, such as High Performance Liquid Chromatography (HPLC), Nuclear Magnetic Resonance (NMR) Spectroscopy, or Infrared (IR)

Spectroscopy. Optionally, if desired, the product can be recrystallized by heating in a solvent, such as methanol, ethanol, isopropanol, and the like, cooling to about 0° C., and filtering and drying the crystals.

For the synthesis of the alkylarylether adduct of phthalonitrile, the molar ratio of $C_{15}$ phenol to 4-nitrophthalonitrile in one embodiment is at least about 1:1, and in one embodiment is no more than about 3:1, and in another embodiment is no more than about 1.5:1, although the molar ratio can be outside of these ranges, and the molar ratio of $C_{15}$ phenol to base in one embodiment is at least about 1:1, and in one embodiment is no more than about 3:1, and in another embodiment is no more than about 1:1 to about 1.5:1, although the molar ratio can be outside of these ranges.

In this embodiment, the second step in the synthesis of the colorant molecules of the present invention entails conversion of the alkylarylether phthalonitrile adduct to the phthalocyanine:

manganese, rhenium, iron, ruthenium, cobalt, rhodium, nickel, palladium, platinum, copper, zinc, cadmium, aluminum, gallium, indium, silicon, germanium, tin, lead, and the like, X is an anion, such as a carboxylate-containing moiety, such as formate, acetate, acetoacetate, propionate, butyrate, benzoate, and the like, an alkoxide, such as methoxide, ethoxide, isopropoxide, or the like, acetyl acetonate, a halide atom, such as fluoride, chloride, bromide, or iodide, sulfate, alkyl sulfonate, aryl sulfonate, nitrate, nitrite, phosphate, and the like, n is a number representing the valence of the metal, and y is an integer of from 0 to 10. Specific examples include (but are not limited to) anhydrous copper chloride, hydrated copper chloride, anhydrous copper acetate, hydrated copper acetate, anhydrous copper sulfate, hydrated copper sulfate, anhydrous copper nitrate, hydrated copper nitrate, anhydrous copper bromide, hydrated copper bromide, and the like, as well as mixtures thereof. The alkylarylether phthalonitrile adduct, metal compound, and a solvent, such as ethylene glycol, amyl

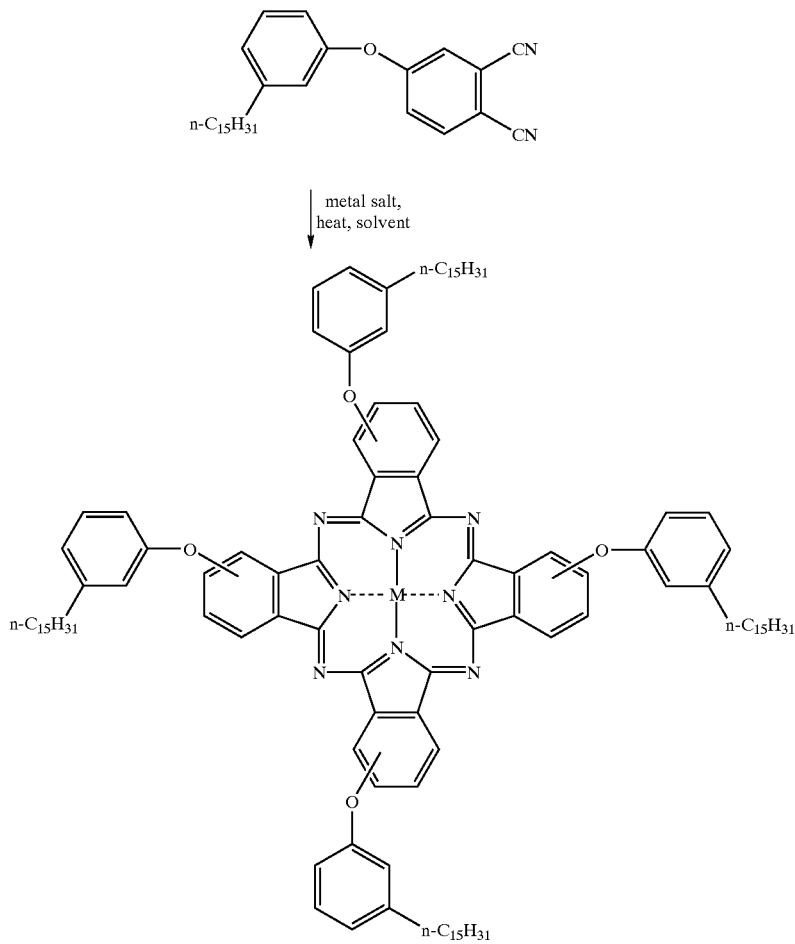

This process can be carried out by reacting the alkylarylether phthalonitrile adduct with a metal compound. Examples of suitable metal compounds include anhydrous and hydrated salts or complexes of the formula $$MX_n \cdot yH_2O$$

wherein M is a metal, such as lithium, sodium, potassium, beryllium, magnesium, calcium, scandium, titanium, zirconium, vanadium, niobium, chromium, molybdenum, alcohol, hexanol, heptanol, tetralin, decalin, ISOPAR® (refined mineral spirits solvents available from Exxon), xylene, tributyl amine, N,N-dimethylaniline, quinoline, 1-chloronaphthalene, trialkanolamines, monoalkyl dialkanolamines, dialkyl monoalkanolamines (such as 2-dimethylaminoethanol, 2-diethylaminoethanol, 2-dimethylamino-1-propanol, and the like), dimethylsulfoxide, N,N-dimethylformamide, N,N-dimethylacetamide, 1-methyl-2-pyrrolidinone, N-cyclohexyl-2-pyrrolidinone, sulfolane, and the like, as well as mixtures thereof, are combined to form the reaction mixture. The solids content of the reaction mixture in one embodiment is at least about 3 parts by weight alkylarylether phthalonitrile adduct per every 100 parts by weight solvent, and in another embodiment is at least about 10 parts by weight alkylarylether phthalonitrile adduct per every 100 parts by weight solvent, and in one embodiment is no more than about 60 parts by weight alkylarylether phthalonitrile adduct per every 100 parts by weight solvent, and in another embodiment is no more than about 30 parts by weight alkylarylether phthalonitrile adduct per every 100 parts by weight solvent, although the solids content can be outside of these ranges. The reaction mixture is heated to reflux. Reflux temperature in one embodiment is at least about 80° C., and in another embodiment is at least about 140° C., and in one embodiment is no more than about 250° C., and in another embodiment is no more than about 190° C., although the temperature can be outside of these ranges. The reaction mixture is refluxed for a period of time in one embodiment of at least about 1 hour, and in another embodiment of at least about 2 hours, and in one embodiment of no more than about 24 hours, and in another embodiment of no more than about 8 hours, although the time can be outside of these ranges. Thereafter, the reaction is cooled to a temperature in one embodiment of at least about 25° C., and in another embodiment of at least about 50° C., and in one embodiment of no more than about 150° C., and in another embodiment of no more than about 100° C., although the temperature can be outside of these ranges, filtered, typically through a filter of paper, glass fiber, polypropylene, GORETEX®, and the like, although other methods of filtration can also be used, and washed with a solvent, such as water, acetone, methyl ethyl ketone, methyl isobutyl ketone, methanol, ethanol, propanol, butanol, acetone, dimethyl formamide, dimethyl sulfoxide, N-methyl pyrrolidinone, sulfolane, and the like, as well as mixtures thereof. If desired, the precipitated blue solids can then again be filtered, slurried with a solvent, such as acetone, methyl ethyl ketone, methyl isobutyl ketone, methanol, ethanol, propanol, butanol, acetone, dimethyl formamide, dimethyl sulfoxide, N-methyl pyrrolidinone, sulfolane, and the like, as well as mixtures thereof, in relative amounts in one embodiment of at least about 3 parts by weight solvent per every 1 part by weight product, and in one embodiment of no more than about 100 parts by weight solvent per every 1 part by weight product, although the relative amounts can be outside of these ranges, for a period of time in one embodiment of at least about 0.5 hour, and in one embodiment of no more than about 24 hours, although the time can be outside of these ranges, and at a temperature in one embodiment of at least about 25° C., and in another embodiment of at least about 50° C., and in one embodiment of no more than about 200° C., and in another embodiment of no more than about 100° C., although the temperature can be outside of these ranges. The product is then filtered again and dried.

If desired, a catalyst or reaction promoter can also be included in the reaction mixture. Examples of suitable catalysts or reaction promoters include trialkanolamines, dialkyl monoalkanolamines, monoalkyl dialkanolamines, and the like, wherein the alkyl groups, which can be connected to the nitrogen atom through a primary, secondary, or tertiary carbon atom, in one embodiment have from 1 to about 6 carbon atoms, and in another embodiment have from 1 to about 3 carbon atoms, although the number of carbon atoms can be outside of these ranges, including (but not limited to) methyl, ethyl, n-propyl, isopropyl, and the like, and wherein the alkanol groups, which can be primary, secondary, or tertiary alkanols and can be connected to the nitrogen atom through a primary, secondary, or tertiary carbon atom, in one embodiment have from about 2 to about 6 carbon atoms, and in another embodiment have from about 2 to about 3 carbon atoms, although the number of carbon atoms can be outside of these ranges, including (but not limited to) 2-hydroxyethyl, 2-hydroxypropyl, 3-hydroxypropyl, and the like, with specific examples of suitable catalysts or reaction promoters including (but not limited to) 2-diethylaminoethanol, 2-dimethylaminoethanol, 2-dimethylamino-1-propanol, and the like, as well as mixtures thereof.

Suitable catalysts or reaction promoters also include ammonia-releasing compounds. Suitable ammonia-releasing compounds are any ammonium salts that release ammonia when heated, including (but not limited to) ammonium carbonate, ammonium carbamate, ammonium bicarbonate, ammonium molybdate, urea, ammonium salts of mono- and dicarboxylic acids, including (but not limited to) formic acid, acetic acid, propionic acid, butyric acid, benzoic acid, oxalic acid, malonic acid, and the like, as well as mixtures thereof. When an ammonia releasing compound is employed as a catalyst or reaction promoter, while not required, in a specific embodiment, the reaction of the alkylarylether phthalonitrile adduct with the copper salt takes place with a two stage temperature-warming profile. The first stage entails heating the reaction mixture to an intermediate temperature, in one embodiment of at least about 80° C., and in one embodiment of no more than about 140° C., although the temperature can be outside of these ranges, and for a period of from time in one embodiment of at least about 0.25 hour, and in one embodiment of no more than about 3 hours, although the time can be outside of these ranges, during which time ammonia gas is slowly released. Thereafter, the reaction mixture is heated to a final temperature, in one embodiment of at least about 120° C., and in another embodiment of at least about 140° C., and in one embodiment of no more than about 250° C., and in another embodiment of no more than about 190° C., although the temperature can be outside of these ranges, and for a period of time in one embodiment of at least about 1 hour, and in another embodiment of at least about 2 hours, and in one embodiment of no more than about 24 hours, and in another embodiment of no more than about 10 hours, although the time can be outside of these ranges.

For the synthesis of the phthalocyanine compound, the molar ratio of 3-pentadecylphenoxy phthalonitrile adduct to metal compound in one embodiment is at least about 2:1, and in another embodiment is at least about 3:1, and in one embodiment is no more than about 10:1, and in another embodiment is no more than about 6:1, although the molar ratio can be outside of these ranges. When a catalyst or reaction promoter is used, the molar ratio of catalyst or reaction promoter to metal compound in one embodiment is at least about 0.1:1, and in another embodiment is at least about 0.5:1, and in one embodiment is no more than about 10:1, and in another embodiment is no more than about 2:1, although the molar ratio can be outside of these ranges.

In one embodiment of the present invention, two or more catalysts or reaction promoters can be used, such as one or more from the class of alkanolamines and one or more from the class of ammonia-releasing compounds, two or more from the class of alkanolamines, two or more from the class of ammonia-releasing compounds, or the like.

Metal-free phthalocyanine can be prepared by treatment of an alkali metal phthalocyanine such as dilithium, disodium, dipotassium, beryllium, magnesium, or calcium phthalocyanine, prepared according to the above process, with a dilute aqueous or alcoholic acid. Examples of suitable acids include (but are not limited to) hydrochloric acid, phosphoric acid, sulfuric acid, nitric acid, sulfonic acids, such as alkylsulfonic, arylsulfonic, arylalkylsulfonic, and alkylarylsulfonic, wherein the alkyl portions thereof can be linear or branched, in one embodiment with from 1 to about 18 carbon atoms, although the number of carbon atoms can be outside of this range, and wherein the aryl portions thereof in one embodiment have from 6 to about 12 carbon atoms, although the number of carbon atoms can be outside of this range, carboxylic acids, such as alkylcarboxylic, arylcarboxylic, arylalkylcarboxylic, and alkylarylcarboxylic, wherein the alkyl portions thereof can be linear or branched, and wherein the carboxylic acid in one embodiment has from 1 to about 24 carbon atoms, although the number of carbon atoms can be outside of this range (such as formic, acetic, propionic, benzoic, and the like), and the like, as well as mixtures thereof. The acid is present in the water or alcohol solution in any desired or effective concentration, in one embodiment of at least about 1 percent by weight acid, and in another embodiment of at least about 2 percent by weight acid, and in one embodiment of no more than about 10 percent by weight acid, and in another embodiment of no more than about 5 percent by weight acid, although the acid concentration can be outside of these ranges. Examples of suitable alcohols include (but are not limited to) methanol, ethanol, propanol, isopropanol, ethylene glycol, and the like, as well as mixtures thereof.

Alternatively, the metal-free phthalocyanine dye can be prepared by heating a concentrated solution of 4-(3-pentadecyl)phenoxyphthalonitrile in a dialkyl monoalkanolamine solvent, wherein the alkyl groups, which can be connected to the nitrogen atom through a primary, secondary, or tertiary carbon atom, in one embodiment have from 1 to about 6 carbon atoms, and in another embodiment have from 1 to about 3 carbon atoms, although the number of carbon atoms can be outside of these ranges, including (but not limited to) methyl, ethyl, n-propyl, isopropyl, and the like, and wherein the alkanol groups, which can be primary, secondary, or tertiary alkanols and can be connected to the nitrogen atom through a primary, secondary, or tertiary carbon atom, in one embodiment have from about 2 to about 6 carbon atoms, and in another embodiment have from about 2 to about 3 carbon atoms, although the number of carbon atoms can be outside of these ranges, including (but not limited to) 2-hydroxyethyl, 2-hydroxypropyl, 3-hydroxypropyl, and the like, with specific examples including 2-dimethylaminoethanol, 2-diethylaminoethanol, 2-dimethylamino-1-propanol, and the like, as well as mixtures thereof, in the presence of an ammonia-releasing compound. The ratio by weight of 4-(3-pentadecyl)phenoxyphthalonitrile to dialkyl monoalkanolamine solvent in one embodiment is at least about 10:80, and in another embodiment is at least about 25:75, and in one embodiment is no more than about 60:40, and in another embodiment is no more than about 50:50, although the relative amounts can be outside of these ranges. Suitable ammonia-releasing compounds include those listed hereinabove with respect to catalysts or reaction promoters. The molar ratio of ammonia-releasing compound to 4-(3-pentadecyl)phenoxyphthalonitrile in one embodiment is at least about 0.1 molar equivalent ammonia-releasing compound per every 1 molar equivalent of 4-(3-pentadecyl)phenoxyphthalonitrile, and in another embodiment is at least about 0.5 molar equivalent ammonia-releasing compound per every 1 molar equivalent of 4-(3-pentadecyl)phenoxyphthalonitrile, and in one embodiment is no more than about 5 molar equivalents ammonia-releasing compound per every 1 molar equivalent of 4-(3-pentadecyl)phenoxyphthalonitrile, and in another embodiment is no more than about 2 molar equivalents ammonia-releasing compound per every 1 molar equivalent of 4-(3-pentadecyl)phenoxyphthalonitrile, although the relative amounts can be outside of these ranges. The mixture can be initially heated to a first temperature, in one embodiment of at least about 50° C., and in another embodiment of at least about 65° C., and in one embodiment of no more than about 130° C., and in another embodiment of no more than about 125° C., although the temperature can be outside of these ranges, for a period of time in one embodiment of at least about 10 minutes, and in another embodiment of at least about 20 minutes, and in one embodiment of no more than about 120 minutes, and in another embodiment of no more than about 60 minutes, although the time can be outside of these ranges, to promote slow release of ammonia, then is subsequently heated to a second temperature which is higher than the first temperature, in one embodiment of at least about 120° C., and in another embodiment of at least about 135° C., and in one embodiment of no more than about 200° C., and in another embodiment of no more than about 170° C., although the temperature can be outside of these ranges, for a period of time in one embodiment of at least about 1 hour, and in another embodiment of at least about 2 hours, and in one embodiment of no more than about 24 hours, and in another embodiment of no more than about 10 hours, although the time can be outside of these ranges. Thereafter, the reaction mixture is cooled, in one embodiment to a temperature of at least about 25° C., and in another embodiment to a temperature of at least about 50° C., and in one embodiment to a temperature of no more than about 125° C., and in another embodiment to a temperature of no more than about 100° C., although the temperature can be outside of these ranges, and the product is separated by filtration or by decantation and washed with a solvent, such as water, acetone, methyl ethyl ketone, methyl isobutyl ketone, methanol, ethanol, propanol, butanol, acetone, dimethyl formamide, dimethyl sulfoxide, N-methyl pyrrolidinone, sulfolane, and the like, as well as mixtures thereof. If desired, the precipitated blue solids can then again be filtered, slurried with a solvent, such as acetone, methyl ethyl ketone, methyl isobutyl ketone, methanol, ethanol, propanol, butanol, acetone, dimethyl formamide, dimethyl sulfoxide, N-methyl pyrrolidinone, sulfolane, and the like, as well as mixtures thereof, in relative amounts in one embodiment of at least about 3 parts by weight solvent per every 1 part by weight product, and in one embodiment of no more than about 100 parts by weight solvent per every 1 part by weight product, although the relative amounts can be outside of these ranges, for a period of time in one embodiment of at least about 0.5 hour, and in one embodiment of no more than about 24 hours, although the time can be outside of these ranges, and at a temperature in one embodiment of at least about 25° C., and in another embodiment of at least about 50° C., and in one embodiment of no more than about 200° C., and in another embodiment of no more than about 100° C., although the temperature can be outside of these ranges. The product is then filtered again and dried.

If desired, the alkylarylether phthalonitrile adduct need not be isolated by addition of precipitant subsequent to its synthesis and prior to its reaction with the metal compound. In this embodiment, the reaction mixture in which the alkylarylether phthalonitrile adduct was formed can, if desired, optionally be filtered to remove any inorganic salts, followed by addition to the reaction mixture of the metal compound and, optionally, any desired reaction promoter. Thereafter, the reaction mixture is heated, to a temperature in one embodiment of at least about 120° C., and in another embodiment of at least about 140° C., and in one embodiment of no more than about 250° C., and in another embodiment of no more than about 190° C., although the temperature can be outside of these ranges, for a period of time in one embodiment of at least about 1 hour, and in another embodiment of at least about 2 hours, and in one embodiment for a period of time of no more than about 24 hours, and in another embodiment of no more than about 8 hours, although the time can be outside of these ranges. The phthalocyanine product thus formed can then be isolated as described hereinabove with respect to the two-step process.

Specific embodiments of the invention will now be described in detail. These examples are intended to be illustrative, and the invention is not limited to the materials, conditions, or process parameters set forth in these embodiments. All parts and percentages are by weight unless otherwise indicated. The purity of the synthesized dye products was determined using standard analytical procedures such as Nuclear Magnetic Resonance Spectroscopy (NMR) and High Performance Liquid Chromatography (HPLC). In addition, the purity of samples of the final phthalocyanine dyes was determined using a spectral strength (SS) measurement determined as follows: A mass of 50 milligrams±2 milligrams of dye was weighed accurately to 0.1 milligram and transferred quantitatively to a 250 milliliter volumetric flask. Approximately 175 milliliters of spectroscopic grade toluene was then added to the flask to dissolve the dye thoroughly. The solution was diluted to the mark with toluene and mixed. Subsequently, 5.00 milliliters of dye solution was pipetted into a second 250 milliliter volumetric flask, which was diluted to the mark with toluene and mixed well. The UV/Visible absorption spectrum of the diluted dye solution was measured in the following way. An HP8452A UV/V is spectrometer or equivalent was used with standard 1 centimeter pathlength quartz cells. A baseline blank consisting of toluene was run. The absorbance of the dilute dye solution was determined at lambda max, which is the maximum absorption wavelength, typically 680 nanometers. The spectral strength was calculated by dividing the absorbance of the dilute dye solution at 680 nanometers by the concentration of the dilute dye solution in grams per milliliter. For the copper dyes, spectral strength values ranging from $1.1 \times 10^5$ to $1.3 \times 10^5$ A*ml/g were judged to be acceptable for phase change ink formulations. The highest value attained, $1.3 \times 10^5$ A*ml/g, is believed to be indicative of about 100 percent pure dye.

EXAMPLE I

Preparation of 4-(3-pentadecylphenoxy) phthalonitrile

To a 500 milliliter 1-necked round bottomed flask equipped with magnetic stirrer was added 45.3 grams (0.15 mole) of CARDOLITE® $NC_{510}$ (predominantly a meta $C_{15}$ alkyl phenol of the formula

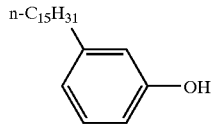

obtained from cashew nut distillation and containing small amounts of naturally occurring isomers thereof, obtained from Cardolite Corporation, Newark, N.J.), 9.3 grams (0.68 mole) of potassium carbonate (obtained from Aldrich Chemical Co., Milwaukee, Wis.), and 260 grams of 1-methyl-2-pyrrolidinone (NMP, anhydrous, obtained from Aldrich Chemical Co.). The mixture was heated in a 90° C. oil bath for one hour. The reaction mixture turned dark brown. Thereafter, 25 grams (0.14 mole) of 4-nitrophthalonitrile (obtained from Aldrich Chemical Co., Milwaukee, Wis.) was added to the reaction mixture and the mixture was maintained at 90° C. for an additional 4 hours. The reaction mixture was then cooled to about 25° C. and quenched in 600 milliliters of deionized water. The precipitated solid was separated by filtration, reslurried with about 600 milliliters of deionized water, and again filtered; this process was repeated until the water used to wash the solid product was of neutral pH. The solids were then dried in air and combined with about 350 grams of isopropanol at 25° C. The resultant suspension was recrystallized by cooling in an ice bath. The crystals were filtered and air dried to give 54.4 grams 87.6 percent yield) of 4-(3-pentadecyl) phenoxyphthalonitrile. The purity of this material as measured by HPLC was about 97 percent.

EXAMPLE II

Preparation of 4-(3-pentadecylphenoxy) phthalonitrile in DMF Solvent

To a 500 milliliter 1-necked round bottomed flask equipped with mechanical stirrer was added 50.25 grams (0.165 mole) of 3-pentadecylphenol, 20.0 grams (0.145 mole) of anhydrous potassium carbonate, 25.0 grams (0.145 mole) of 4-nitrophthalonitrile, and 250 grams of dimethylformamide (DMF, obtained from Caledon Labs, Georgetown Ontario, Canada). The mixture was heated to 90° C. for 2 hours using a heating mantle. The reaction mixture turned dark brown. The reaction mixture was cooled to about 60° C., then was quenched by pouring slowly into 1 liter of deionized water. The precipitated beige solid was separated by filtration, then was reslurried and filtered using about 600 milliliter portions of deionized water, until the water used to wash the solid product was of neutral pH. The product was then twice reslurried in 600 milliliters of methanol, filtered, and vacuum dried at 40° C. to give 42.6 grams (68 percent yield) of 4-(3-pentadecyl) phenoxyphthalonitrile. The purity of this material as measured by HPLC was about 98 percent.

EXAMPLE III

Preparation of 4-(3-pentadecylphenoxy) phthalonitrile in NMP

To a 5 liter 1-necked round bottomed flask equipped with mechanical stirrer was added 502.5 grams (1.65 mole) of 3-pentadecylphenol, 200 grams (1.45 mole) of potassium carbonate, and 2,000 grams of 1-methyl-2-pyrrolidinone (anhydrous; obtained from Aldrich Chemical Co.). The mixture was heated to 90° C. for 2 hours using a heating mantle. The reaction mixture turned dark brown. Thereafter, 250.0 grams (1.45 mole) of 4-nitrophthalonitrile (obtained from Sigma-Aldrich) was added and the mixture was maintained at 90° C. for an additional 2 hours. The hot reaction mixture was then quenched by slowly pouring it into 3 liters of deionized water. The precipitated beige suspension was stirred until it had cooled to room temperature, then was filtered. The solid was then reslurried and filtered, using about 6 liter portions of deionized water, until the water used to wash the solid product was of neutral pH. The solid was then twice reslurried in 4 liters of methanol, filtered, and vacuum dried at 40° C. to give 519.8 grams (84 percent yield) of 4-(3-pentadecyl) phenoxyphthalonitrile. The purity of this material as measured by HPLC was more than 89 percent.

EXAMPLE IV

Preparation of 4-(3-pentadecylphenoxy) phthalonitrile in DMSO solvent

To a 5 liter 1-necked round bottomed flask equipped with mechanical stirrer was added 502.5 grams (1.65 mole) of 3-pentadecylphenol, 200 grams (1.45 mole) of anhydrous potassium carbonate, 250.0 grams (1.45 mole) of 4-nitrophthalonitrile, and 2,000 grams of dimethylsulfoxide (DMSO, obtained from Caledon Labs, Georgetown Ontario, Canada). The mixture was heated to 90° C. for 3 hours using a heating mantle. The reaction mixture turned dark brown. The reaction mixture was then cooled to 80° C., and was quenched by slowly pouring 3 liters of deionized water into the flask. The precipitated beige solid was stirred until the suspension had cooled to room temperature, then was separated by filtration. It was then twice slurried and filtered using about 6 liter portions of deionized water. The wet cake was then stirred for 1 hour in 6 liters of 2 percent aqueous hydrochloric acid, which served to dissolve small amounts of insoluble metal carbonate contaminants, then was filtered. It was slurried, filtered, and reslurried in 6 liter portions of deionized water until the water used to wash the solid product was of neutral pH. The solids were then twice slurried in 4 liters of methanol, filtered, and vacuum dried at 40° C. to give 558.4 grams (90 percent yield) of 4-(3-pentadecyl) phenoxyphthalonitrile. The purity of this material as measured by HPLC was over 98 percent.

EXAMPLE V

Copper Dye Preparation in Hexanol

A mixture of 52 grams (0.12 mole) of dried solid crystals of 4-(3-pentadecyl) phenoxyphthalonitrile (prepared as described in Example I), 4.1 grams (0.030 mole) of anhydrous copper (II) chloride (obtained from Aldrich Chemical Co.), and 600 grams of hexanol (anhydrous) (obtained from Aldrich Chemical Co.) in a 1 liter kettle equipped with mechanical stirrer, temperature controller, and condenser was stirred and heated. The color of the reaction mixture eventually turned to blue upon heating to reflux (about 160° C.). The reaction mixture was refluxed and stirred for 3 hours. Thereafter the reaction mixture was quenched in 1,200 milliliters of methanol. The precipitated blue solid thus obtained was filtered and then slurried with 150 milliliters of acetone. The solids were again filtered and dried. Yield of the product, which is believed to be mixed isomers of the formula

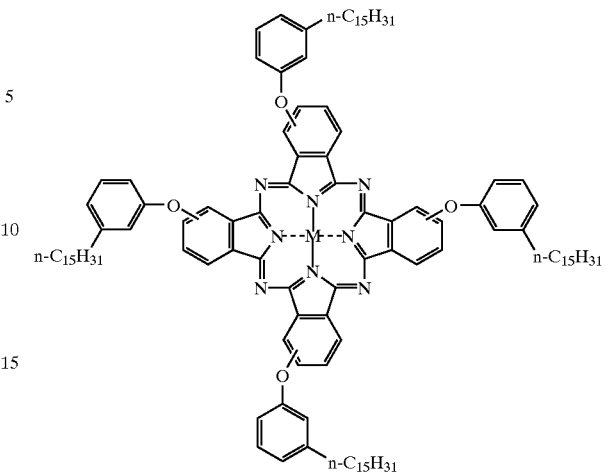

was 24.1 grams (about 45 percent). UV/Vis (toluene): 683 nanometers.

EXAMPLE VI

Copper Dye Preparation in NMP (no catalyst)

A solution of 4-(3-pentadecyl)phenoxyphthalonitrile (4.74 grams, 0.11 mole; prepared as in Example III) in 25 milliliters of NMP containing 0.50 grams (0.0025 mole) of copper(II) acetate monohydrate was stirred and heated to 150° C. After 15 minutes, a deep, dark green color developed. The mixture was stirred for 3 hours at 150° C., and then cooled to room temperature and filtered. The resultant product was washed with 40 milliliters of acetone and then dried in air for 24 hours to give 2.49 grams (56 percent) of the copper phthalocyanine dye as dark blue, waxy, globular lumps.

EXAMPLE VII

Copper Dye Preparation in NMP with Ammonium Acetate

A mixture of 4-(3-pentadecyl) phenoxyphthalonitrile (25.8 grams, 0.060 mole), copper(II) acetate dihydrate (3.0 grams, 0.015 mole), and ammonium acetate (9.2 grams, 0.12 mole) in 100 milliliters of NMP was stirred and heated to 120° C. Slow gas evolution was observed, and after 5 minutes, a deep, dark blue color developed. After 30 minutes at 120° C. the reaction mixture was heated to 180° C. for 1 hour. NMP (50 milliliters) was then added and the mixture was stirred and reheated to 180° C., followed by cooling with stirring to room temperature. The product was then filtered and the solid was washed in the filter funnel with 2×100 milliliter portion of DMF. It was then stirred in 200 milliliters of acetone at 50° C. and subsequently filtered. This acetone treatment was repeated, and the solid was dried at 60° C. overnight to give the product as a coarse powder (19.9 grams, 74 percent). The spectral strength of this material was $1.27 \times 10^5$ A*ml/g, which is indicative of high (i.e. about 98 percent) purity.

EXAMPLE VIII

Copper Dye Preparation in NMP with Dimethylaminoethanol

A solution of 60.8 grams (0.14 mole) of 4-(3-pentadecyl) phenoxyphthalonitrile in 195 milliliters of NMP in a 500 milliliter flask fitted with a mechanical stirrer, maintained under a nitrogen atmosphere, was treated with 6.24 grams (0.031 mole) of copper(II) acetate monohydrate, and 6.24 grams (0.070 mole) of 2-dimethylaminoethanol (DMAE). The mixture was stirred and heated at 180° C. for 6 hours, then was cooled to 80° C. The mixture was then filtered, and the solid was washed in the filter with 120 milliliters of NMP. The solid was then slurry-washed and filtered three times with 120 milliliter portions of methyl ethyl ketone. Drying for 48 hours at 30° C. under vacuum gave the product as a coarse dark blue powder (44 grams, 80 percent). The spectral strength of this dye was $1.28 \times 10^5$ A*mL/g, indicating a purity of over 98 percent.

EXAMPLE IX

Copper Dye Preparation in NMP

A solution of 3-pentadecylphenol (16.75 grams, 0.055 mole) in 90 milliliters of NMP containing anhydrous potassium carbonate (7.6 grams, 0.055 mole) was stirred and heated to 100° C. After 10 minutes, 4-nitrophthalonitrile (8.65 grams, 0.050 mole) was added and the mixture was heated at 100° C. for a further 40 minutes. Copper(II) acetate monohydrate (2.50 grams, 0.050 mole) and ammonium acetate (3.9 grams, 0.050 mole) were then added and the mixture was heated to 135° C. for 30 minutes, followed by heating to 170° C. DMAE (10 milliliters) was then added and the mixture was stirred at 170° C. for 2.25 hours. The mixture was then cooled to room temperature and the product was washed in the filter funnel with 50 milliliters of DMF, followed by washing with 50 milliliters of methanol. The product was then slurried in 100 milliliters of methanol, followed by filtration and drying at 60° C. to give 9.2 grams (41 percent) of the dye as a fine, bluish black solid.

EXAMPLE X

Copper Dye Preparation in NMP

A mixture of 3-pentadecylphenol (182.7 grams, 0.72 mole) and anhydrous potassium carbonate (91 grams, 0.66 mole) in 650 milliliters of NMP in a 2,000 milliliter Erlenmeyer flask was stirred and heated to 90° C. 4-Nitrophthalonitrile (104 grams, 0.60 mole) was then added and the mixture was heated at 100° C. for 1 hour. The resultant suspension was cooled to 50° C. and was filtered. The solid was washed with 4×50 milliliter portions of NMP. (The solid was then further washed in the funnel with 4×50 milliliter portions of acetone and was dried at 60° C. to give 91 grams of white hygroscopic solid, which is believed to be a mixture of potassium bicarbonate and potassium nitrite, although this conclusion was not confirmed.) The combined filtrate and NMP wash solvent was stirred in a 2,000 milliliter Erlenmeyer flask and was treated with copper(II) acetate monohydrate (30.0 grams, 0.15 mole), ammonium acetate (24 grams, 0.30 mole), and DMAE (60 milliliters, 0.60 mole). The mixture was heated to 120° C. for 15 minutes, and subsequently heated at 180° C. for 3 hours. (A dark blue color developed when the reaction temperature reached about 165° C.) The reaction mixture was cooled to 70° C., and then was filtered. The solid was washed on the filter funnel with 2×200 milliliter portions of NMP, followed by washing with 200 milliliters of acetone. The solid was stirred in 700 milliliters of acetone at 50° C. for 1 hour, then was filtered and dried at 60° C. to give 178.5 grams (67 percent) of dye as fine dark blue powder. The spectral strength of the product was $1.11 \times 10^5$ A*mL/g, indicative of about 86 percent purity.

EXAMPLE XI

Zinc Dye Preparation

A mixture of 4-(3-pentadecyl)phenoxyphthalonitrile (9.50 grams, 0.022 mole), zinc acetate dihydrate (1.10 gram, 0.0050 mole, obtained from Aldrich Chemical Co.), and DMAE (5 milliliters) in NMP (45 milliliters) was stirred and heated to 175° C. The resultant deep dark blue-green solution was heated at 175° C. for 3 hours, then was cooled to room temperature. Addition of methanol to the solution caused precipitation of a sticky solid, which was separated by decantation. The solid was washed in the flask with 2×25 milliliter portions of acetone, then was dried to give 5.0 grams (56 percent) of the zinc dye, of the formula

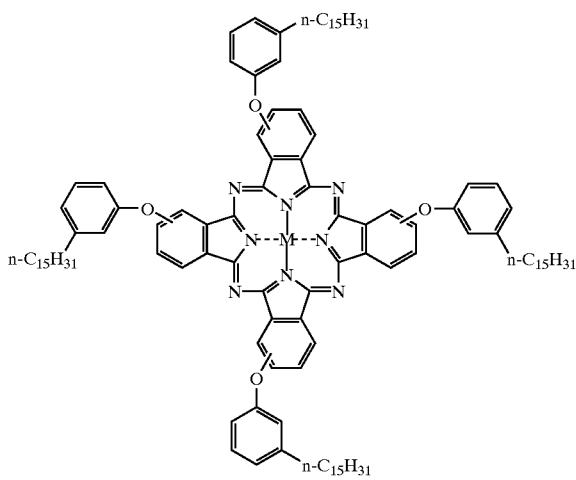

as sticky blue solid. UV/Vis (toluene): 682 nanometers.

EXAMPLE XII

Metal-Free Dye Preparation

To a solution of 4-(3-pentadecyl)phenoxyphthalonitrile (34 grams, 0.11 mole) in 50 milliliters of 2-dimethylaminoethanol was added ammonium acetate (7.7 grams, 0.10 mole). The mixture was stirred and heated to 120° C. for 15 minutes, followed by heating at reflux (140° C.) for 6 hours. Thereafter, the dark blue-green solution was diluted with 100 milliliters of DMF and was cooled to 80° C. The sticky lumps of product were separated by decanting and were washed with 4×25 milliliter portions of DMF. Trituration with 20 milliliters of acetone, followed by stirring in 100 milliliters of acetone, separation (by decanting), and drying at 60° C. gave the metal-free dye as lumps of dark blue, gummy solid (8.0 grams, 19 percent yield). UV/Vis (toluene): 702, 667 nanometers (this intense doublet is diagnostic of a metal-free phthalocyanine).

EXAMPLE XIII

Nickel Dye Preparation

To a solution of 4-(3-pentadecyl)phenoxyphthalonitrile (34 grams, 0.11 mole) in 200 milliliters of NMP was added nickel(II) acetate tetrahydrate (6.22 grams, 0.025 mole) and ammonium acetate (7.7 grams, 0.10 mole). The mixture was stirred and heated at 120° C. for 20 minutes, followed by heating at 170° C. for 2 hours. A dark blue color formed when the reaction mixture reached 150° C. The mixture was cooled to 100° C., followed by filtration and washing of the solid in the funnel with 3×50 milliliter portions of DMF. The product was then slurried in 200 milliliters of acetone for 14 hours, followed by separation by decantation. The isolated product was a sticky globular solid (22.0 grams, 49 percent yield). UV/Vis (toluene): 673 nanometers.

EXAMPLE XIV

Cobalt Dye Preparation

A mixture of cobaltous chloride (3.25 grams, 0.025 mole), 4(-3-pentadecyl)phenoxyphthalonitrile (34 grams, 0,11 mole) and DMAE (10 milliliters, 0.10 mole) in 100 milliliters of NMP in a 250 milliliter Erlenmeyer flask was stirred and heated to 180° C. A dark blue-green color was observed at 140° C. The mixture was stirred at 180° C. for 2 hours, followed by addition of 100 milliliters of DMF. On cooling to room temperature, the product separated as sticky balls, which were separated by decanting and washed, first with 3×25 milliliter portions of DMF, then with 25 milliliters of acetone. The product was then stirred in 100 milliliters of acetone at 50° C. for 1 hour, followed by separation and drying in air to give the product as dark blue balls (15.0 grams, 34 percent yield). UV/Vis (toluene): 673 nanometers.

Comparative Example A

Preparation and Testina of 4-dodecylphenoxy Copper Phthalocyanine Dye

To a solution of 4-n-dodecylphenol (14.4 grams, 0.055 mole; obtained from Aldrich Chemical Co., Milwaukee, Wis.) in 90 milliliters of NMP was added 7.6 grams (0.055 mole) of anhydrous potassium carbonate. The mixture was stirred and heated to 100° C. After 10 minutes, 4-nitrophthalonitrile (8.65 grams, 0.0050 mole) was added. After 40 additional minutes at 100° C., copper(II) acetate monohydrate (2.50 grams, 0.00125 mole) and ammonium acetate (3.9 grams, 0.050 mole) were added and the mixture was heated to 170° C. After 10 additional minutes, 2-dimethylaminoethanol (10 milliliters) was added, which caused the instant formation of a dark greenish blue color. The mixture was heated at 170° for 2.25 hours, then was cooled to room temperature. The mixture was filtered and the product was washed in the filter funnel with 2×50 milliliter portions of dimethyl formamide. The product was then slurried in 100 milliliters of methanol, followed by filtering and drying at 60° C. to give 6.5 grams (32 percent yield) of blue powder, which was believed to be a mixture of the 4 possible isomers of the tetrakis(4-n-dodecyl) phenoxyphthalocyanine shown below:

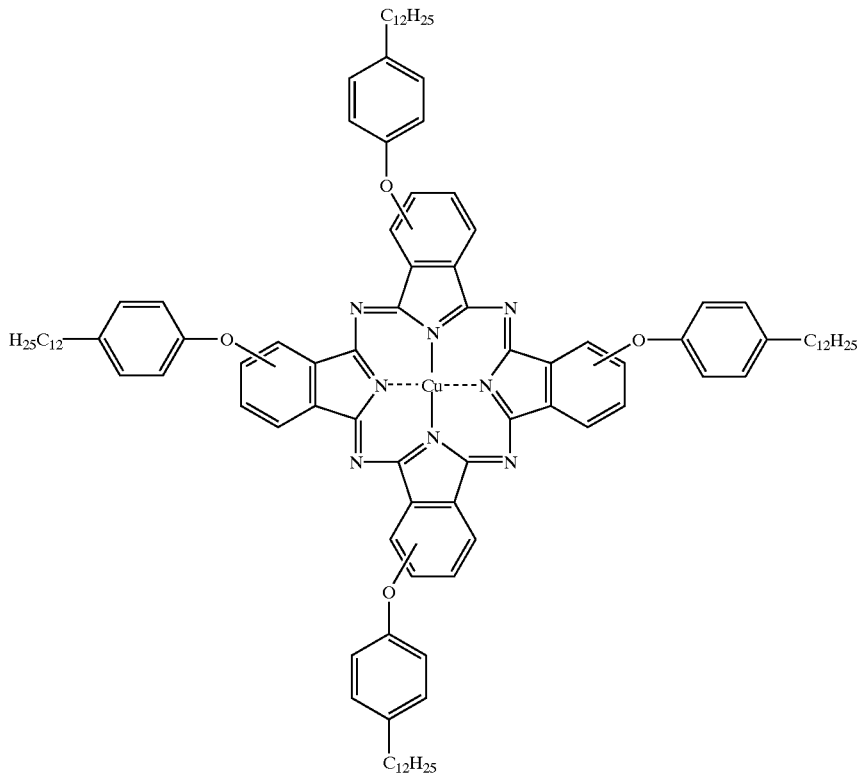

A phase change ink vehicle was prepared as follows. In a stainless steel beaker were combined 140 grams of polyethylene wax (PE 655, obtained from Baker Petrolite, Tulsa, Okla., of the formula $CH_3(CH_2)_{50}CH_3$), 32 grams of stearyl stearamide wax (KEMAMIDE® S-180, obtained from Crompton Corporation, Greenwich, Conn., about 40 grams of a tetraamide resin obtained from the reaction of one equivalent of dimer acid with two equivalents of ethylene diamine and UNICID® 700 (obtained from Baker Petrolite, Tulsa, Okla., a carboxylic acid derivative of a long chain alcohol), prepared as described in Example 1 of U.S. Pat. No. 6,174,937, the disclosure of which is totally incorporated herein by reference, 30 grams of a urethane resin obtained from the reaction of two equivalents of ABITOL® E hydroabietyl alcohol (obtained from Hercules Inc., Wilmington, Del.) and one equivalent of isophorone diisocyanate, prepared as described in Example 1 of U.S. Pat. No. 5,782,966, the disclosure of which is totally incorporated herein by reference, 12 grams of a urethane resin that was the adduct of three equivalents of stearyl isocyanate and a glycerol-based alcohol prepared as described in Example 4 of U.S. Pat. No. 6,309,453, the disclosure of which is totally incorporated herein by reference, and 0.5 gram of NAUGUARD® 445 antioxidant (obtained from Uniroyal Chemical Co., Middlebury, Conn.). The materials were melted together at a temperature of about 140° C. in an oven, then blended by stirring in a temperature controlled mantle at about 135° C. for about 0.5 hour.

A 0.5 gram sample of the copper dye prepared as described in Example X was stirred in 9.5 grams of the above ink base in a 2.5 inch diameter aluminum weighing pan on a hotplate-stirrer heated to a surface temperature of 150° C. The mixture was stirred for 30 minutes using a magnetic stirrer. A sample of this molten ink was spread on Hammermill Laser Print paper using a doctor blade with a 10 micron gap. The resulting swatch was a uniform blue color with an optical density of about 1.2.

The above test was repeated using 0.5 grams of the 4-dodecylphenoxy copper phthalocyanine dye from this Comparative Example. The resultant ink swatch was not of a uniform color, and revealed poor solubility of the dye as evidenced by low color strength (optical density of about 0.64) and dark streaks caused by undissolved dye clumps in the ink.

Comparative Example B

Preparation and Testing of Tetra-t-Butyl Metal-Free Phthalocyanine Dye

Sodium metal (0.10 gram, 4.3 mmole) was dissolved in 200 milliliters of n-amyl alcohol. To the solution was then added 1.84 grams (10 mmole) of 4-t-butylphthalonitrile (obtained from TCI America, Portland, Oreg.). The solution was heated at reflux (about 138° C.) for 4.25 hours. The mixture was then cooled to room temperature and was treated with methanol (70 milliliters) and water (5 milliliters), which converted the intermediate disodium phthalocyanine to the metal-free form. The product was filtered, was washed with 50 milliliters of methanol and 50 milliliters of water, and then was dried in air to give 1.28 grams (66 percent) of mixed isomers of tetra(t-butyl) metal-free phthalocyanine. UV/Vis (toluene): 700, 662 nm.

A test ink was formulated with this dye by the method described in Comparative Example A with a 0.25 gram portion of the dye from this Comparative Example (note: the molecular weight of this dye is about half that of the dye of Example X). The resultant ink swatch revealed poor solubility of the test dye as evidenced by dark streaks caused by undissolved dye clumps in the ink.

Comparative Example C

Preparation and Testing of Tetra-t-Butyl Zinc Phthalocyanine Dye

Tetra-t-butyl metal-free phthalocyanine (1.48 grams, 2 mmole) in 30 milliliters of anhydrous methanol was treated with a solution of lithium methoxide in methanol (1.0 molar solution, obtained from Aldrich Chemical Co.; 5 milliliters, 5 mmoles). The resultant solution of dilithium phthalocyanine was stirred under an argon atmosphere for 1 hour, and then was treated with anhydrous zinc chloride (0.30 gram, 2.2 mmoles) in small portions with vigorous stirring. The resultant suspension was stirred for 1 hour, and then was filtered and the solid washed with 4×10 milliliter portions of methanol, followed by drying at 60° C. to give tetra-t-butyl zinc phthalocyanine as a dark blue powder (1.38 gram, 86 percent). Anal. Calcd. for $C_{48}H_{48}N_8Zn$: C, 71.86; H, 6.03; N, 13.97. Found: C, 71.97; H, 7.65; N, 13.98. UV/Vis (toluene): 677 nm.

A test ink was formulated with this dye by the method described in Comparative Example A with a 0.25 gram portion of the dye from this Comparative Example (note: the molecular weight of this dye is about half that of the dye of Example X). The resultant ink swatch revealed poor solubility of the test dye as evidenced by dark streaks caused by undissolved dye clumps in the ink.

EXAMPLE XV

A phase change ink according to the present invention was prepared as follows. In a stainless steel beaker were combined 140 grams of polyethylene wax (PE 655, obtained from Baker Petrolite, Tulsa, Okla., of the formula $CH_3(CH_2)_{50}CH_3$), 32 grams of stearyl stearamide wax (KEMAMIDE® S-180, obtained from Crompton Corporation, Greenwich, Conn.), about 40 grams of a tetraamide resin obtained from the reaction of one equivalent of dimer acid with two equivalents of ethylene diamine and UNICID® 700 (obtained from Baker Petrolite, Tulsa, Okla., a carboxylic acid derivative of a long chain alcohol), prepared as described in Example 1 of U.S. Pat. No. 6,174,937, the disclosure of which is totally incorporated herein by reference, 30 grams of a urethane resin obtained from the reaction of two equivalents of ABITOL® E hydroabietyl alcohol (obtained from Hercules Inc., Wilmington, Del.) and one equivalent of isophorone diisocyanate, prepared as described in Example 1 of U.S. Pat. No. 5,782,966, the disclosure of which is totally incorporated herein by reference, 12 grams of a urethane resin that was the adduct of three equivalents of stearyl isocyanate and a glycerol-based alcohol prepared as described in Example 4 of U.S. Pat. No. 6,309,453, the disclosure of which is totally incorporated herein by reference, and 0.5 gram of NAUGUARD® 445 antioxidant (obtained from Uniroyal Chemical Co., Middlebury, Conn.). The materials were melted together at a temperature of about 140° C. in an oven, then blended by stirring in a temperature controlled mantle at about 135° C. for about 0.5 hour. To this mixture was then added about 13 grams of the copper phthalocyanine compound prepared as described in Example I. After stirring for about 3 additional hours, the cyan ink thus formed was filtered through a heated MOTT® apparatus (obtained from Mott Metallurgical) using #3 Whatman filter paper and a pressure of about 15 pounds per square inch. The filtered phase change ink was poured into molds and allowed to solidify to form ink sticks.

The cyan phase change ink thus prepared exhibited a viscosity of about 10.6 centipoise as measured by a Rheometrics cone-plate viscometer at about 140° C., a melting point of about 80° C. as measured by differential scanning calorimetry using a DuPont 2100 calorimeter, a glass transition temperature ($T_g$) of about 14° C., and a spectral strength, determined by using a spectrophotographic procedure based on the measurement of the colorant in solution by dissolving the solid ink in toluene and measuring the absorbance using a Perkin Elmer Lambda 2S UV/VIS spectrophotometer, of about 4535 milliliters absorbance per gram at 681 nanometers.

Comparative Example D

A phase change ink was prepared as follows. In a stainless steel beaker were combined 400 grams of polyethylene wax (PE 655, obtained from Baker Petrolite, Tulsa, Okla., of the formula $CH_3(CH_2)_{50}CH_3$), 100 grams of stearyl stearamide wax (KEMAMIDE® S-180, obtained from Crompton Corporation, Greenwich, Conn.), 152 grams of a tetraamide resin obtained from the reaction of one equivalent of dimer acid with two equivalents of ethylene diamine and UNICID® 700 (obtained from Baker Petrolite, Tulsa, Okla., a carboxylic acid derivative of a long chain alcohol), prepared as described in Example 1 of U.S. Pat. No. 6,174,937, the disclosure of which is totally incorporated herein by reference, 100 grams of a urethane resin obtained from the reaction of two equivalents of ABITOL® E hydroabietyl alcohol (obtained from Hercules Inc., Wilmington, Del.) and one equivalent of isophorone diisocyanate, prepared as described in Example 1 of U.S. Pat. No. 5,782,966, the disclosure of which is totally incorporated herein by reference, 42 grams of a urethane resin that was the adduct of three equivalents of stearyl isocyanate and a glycerol-based alcohol, prepared as described in Example 4 of U.S. Pat. No. 6,309,453, the disclosure of which is totally incorporated herein by reference, and 0.5 gram of NAUGUARD® 445 antioxidant (obtained from Uniroyal Chemical Co., Middlebury, Conn.). The materials were melted together at a temperature of about 140° C. in an oven, then blended by stirring in a temperature controlled mantle at about 135° C. for about 0.5 hour. To this mixture was then added about 23 grams of a commercially available copper phthalocyanine dye (SAVINYL BLUE GLS, obtained from Clariant Corporation, Coventry, R.I.). After stirring for about 3 additional hours, the cyan ink thus formed was filtered through a heated MOTT® apparatus (obtained from Mott Metallurgical) using #3 Whatman filter paper and a pressure of about 15 pounds per square inch. The filtered phase change ink was poured into molds and allowed to solidify to form ink sticks.

The cyan phase change ink thus prepared exhibited a viscosity of about 10.6 centipoise as measured by a Rheometrics cone-plate viscometer at about 140° C., a melting point of about 80° C. as measured by differential scanning calorimetry using a DuPont 2100 calorimeter, a glass transition temperature (Tg) of about 15° C., and a spectral strength, determined by using a spectrophotographic procedure based on the measurement of the colorant in solution by dissolving the solid ink in butanol and measuring the absorbance using a Perkin Elmer Lambda 2S UV/VIS spectrophotometer, of about 1224 milliliters absorbance per gram at about 670 nanometers.

The cyan ink thus prepared was placed in a XEROX® PHASER 860 printer, which uses a printing process wherein the ink is first jetted in an imagewise pattern onto an intermediate transfer member followed by transfer of the imagewise pattern from the intermediate transfer member to a final recording substrate. The ink was printed with a printhead temperature of 138° C. and an intermediate transfer drum temperature of 64° C. with HAMMERMILL LASERPRINT® paper (obtained from International Paper, Memphis, Tenn.).

Comparative Example E

A phase change ink was prepared as follows. In a stainless steel beaker were 500 grams of stearyl stearamide wax (KEMAMIDE® S-180, obtained from Crompton Corporation, Greenwich, Conn.) about 150 grams of a tetraamide resin (UNIREZ® 2970, Arizona Chemical Company, Jacksonville, Fla.), 100 grams of a urethane resin obtained from the reaction of two equivalents of ABITOL® E hydroabietyl alcohol (obtained from Hercules Inc., Wilmington, Del.) and one equivalent of isophorone diisocyanate, prepared as described in Example 1 of U.S. Pat. No. 5,782,966, the disclosure of which is totally incorporated herein by reference, 51 grams of a urethane resin that was the adduct of three equivalents of stearyl isocyanate and a glycerol-based alcohol, prepared as described in Example 4 of U.S. Pat. No. 6,309,453, the disclosure of which is totally incorporated herein by reference, and 0.5 gram of NAUGUARD® 445 antioxidant (obtained from Uniroyal Chemical Co., Middlebury, Conn.). The materials were melted together at a temperature of about 140°C in an oven, then blended by stirring in a temperature controlled mantle at about 135°C for about 0.5 hour. To this mixture was then added about 23 grams of a commercially available copper phthalocyanine dye (SAVINYL BLUE GLS, obtained from Clariant Corporation, Coventry, R.I.). After stirring for about 3 additional hours, the cyan ink thus formed was filtered through a heated MOTT® apparatus (obtained from Mott Metallurgical) using #3 Whatman filter paper and a pressure of about 15 pounds per square inch. The filtered phase change ink was poured into molds and allowed to solidify to form ink sticks.

The cyan phase change ink thus prepared exhibited a viscosity of about 10.6 centipoise as measured by a Rheometrics cone-plate viscometer at about 140° C., a melting point of about 80° C. as measured by differential scanning calorimetry using a DuPont 2100 calorimeter, a glass transition temperature (Tg) of about 5° C., and a spectral strength, determined by using a spectrophotographic procedure based on the measurement of the colorant in solution by dissolving the solid ink in butanol and measuring the absorbance using a Perkin Elmer Lambda 2S UV/VIS spectrophotometer, of about 3332 milliliters absorbance per gram at about 670 nanometers.

The cyan ink thus prepared was placed in a XEROX® PHASER 860 printer, which uses a printing process wherein the ink is first jetted in an imagewise pattern onto an intermediate transfer member followed by transfer of the imagewise pattern from the intermediate transfer member to a final recording substrate. The ink was printed with a printhead temperature of 138° C. and an intermediate transfer drum temperature of 64° C. with HAMMERMILL LASERPRINT® paper (obtained from International Paper, Memphis, Tenn.).

Examination of the spectral strength values of the inks of Comparative Example D and Comparative Example E clearly indicates a large difference in the solubility of conventional copper phthalocyanine dye such as SAVINYL BLUE GLS between the respective carrier compositions. Comparison of the carrier compositions of Example D and Example XV reveals only small differences in the proportions of carrier composition components.

Transmission spectra for the phase change inks of Example XV, Comparative Example D, and Comparative Example E were evaluated on a commercially available spectrophotometer, the ACS SPECTRO-SENSOR II, in accordance with the measuring methods stipulated in ASTM 1E805 (Standard Practice of Instrumental Methods of Color or Color Difference Measurements of Materials) using the appropriate calibration standards supplied by the instrument manufacturer. For purposes of verifying and quantifying the overall colorimetric performance of the inks, measurement data were reduced, via tristimulus integration, following ASTM E308 (Standard Method for Computing the Colors of Objects using the CIE System) in order to calculate the 1976 CIE L* (Lightness), a* (redness-greenness), and b* (yellowness-blueness) CIELAB values for each phase change ink sample. In addition, the values for CIELAB Psychometric Chroma, $C^*_{ab}$, and CIELAB Psychometric Hue Angle, were calculated according to publication CIE15.2, Colorimetry (Second Edition, Central Bureau de la CIE, Vienna, 1986).

The CIE L*a*b* color coordinates of printed swatches of the inks prepared in Example XV, Comparative Example D, and Comparative Example E are listed in the table below.

| Example | L* | a* | b* | C* |
|---|---|---|---|---|
| XV | 58 | −33 | −24 | 41 |
| D | 78 | −24 | −23 | 33 |
| E | 64 | −24 | −39 | 46 |

As the data indicate, the ink of Comparative Example D exhibits a low tinctoral strength relative to Example XV, demonstrating the unsuitability of the commercially available copper phthalocyanine dye in this ink.

Comparative Example F

A phase change ink was prepared according to the method described in Example 4 of U.S. Pat. No. 5,919,839, the disclosure of which is totally incorporated herein by reference. The cyan phase change ink thus prepared exhibited a viscosity of about 10.6 centipoise as measured by a Rheometrics cone-plate viscometer at about 140° C., a melting point of about 80° C. as measured by differential scanning calorimetry using a DuPont 2100 calorimeter, a glass transition temperature (Tg) of about 10° C., and a spectral strength, determined by using a spectrophotographic procedure based on the measurement of the colorant in solution by dissolving the solid ink in butanol and measuring the absorbance using a Perkin Elmer Lambda 2S UV/VIS spectrophotometer, of about 1400 milliliters absorbance per gram at about 628 nanometers.

The cyan ink thus prepared was placed in a XEROX® PHASER 860 printer, which uses a printing process wherein the ink is first jetted in an imagewise pattern onto an intermediate transfer member followed by transfer of the imagewise pattern from the intermediate transfer member to a final recording substrate. The ink was printed with a printhead temperature of 138° C. and an intermediate transfer drum temperature of 64° C. with HAMMERMILL LASERPRINT® paper (obtained from International Paper, Memphis, Tenn.).

Swatches of printed cyan solid inks from Example XV and of printed cyan solid inks from this Comparative Example were irradiated for 100 hours with a xenon lamp. The color difference of each irradiated sample relative to its respective un-irradiated control swatch was determined according to the methods described hereinabove for obtaining CIELAB values. Color differences were determined following ASTM D2244–89 (Standard Test Method for Calculation of Color Differences From instrumentally Measured Color Coordinates). The table below shows the initial printed color measurements in CIE L*a*b* color space of the sample swatches and their respective values after 100 hours of xenon irradiation:

| Exam- | Before Irradiation | | | After Irradiation | | | Color Difference |
|---|---|---|---|---|---|---|---|
| ple | L* | a* | b* | L* | a* | b* | (ΔE) |
| XV | 54 | −37 | −31 | 55 | −41 | −26 | 6 |
| F | 57 | −22 | −41 | 95 | −2 | 3 | 61 |

As the data indicate, the color stability upon xenon lamp irradiation of the swatch prepared with the ink of Example XV is vastly superior to that of the ink prepared in Comparative Example F, as indicated by the lower ΔE value for Example XV.

Swatches of printed cyan solid inks from Example XV and of printed cyan solid inks from this Comparative Example were placed in an Atlas Fade-ometer (Atlas Electric Devices Co, Chicago, Ill.) and irradiated for 100 hours at a lamp power of about 1,800 watts. The color difference of each irradiated sample relative to its respective un-irradiated control swatch was determined according to the methods described hereinabove for obtaining CIELAB values. Color differences were determined following ASTM D2244–89 (Standard Test Method for Calculation of Color Differences From instrumentally Measured Color Coordinates). The table below shows the initial printed color measurements in CIE L*a*b* color space of the sample swatches and their respective values after 100 hours in the Atlas Fade-ometer:

| Exam- | Before Irradiation | | | After Irradiation | | | Color Difference |
|---|---|---|---|---|---|---|---|
| ple | L* | a* | b* | L* | a* | b* | (ΔE) |
| XV | 54 | −37 | −31 | 54 | −39 | −31 | 1.4 |
| F | 57 | −22 | −41 | 61 | −15 | 22 | 21 |

As the data indicate, the color stability upon fluorescent irradiation of the swatch prepared with the ink of Example XV is vastly superior to that of the ink prepared in Comparative Example F, as indicated by the lower ΔE value for Example XV.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:
1. A process for preparing a colorant of the formula

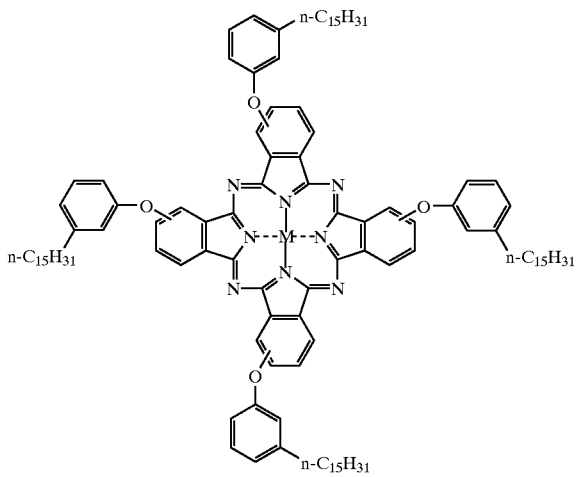

wherein M is an atom or group of atoms capable of bonding to the central cavity of a phthalocyanine molecule, wherein axial ligands optionally can be attached to M, which comprises (a) reacting 3-n-pentadecylphenol with 4-nitrophthalonitrile in the presence of a base to form an alkylarylether adduct of phthalonitrile; and (b) reacting the alkylarylether adduct of phthalonitrile with either (i) a metal compound, or (ii) an ammonia-releasing compound in the presence of an alkanolamine solvent, or (iii) mixtures of (i) and (ii), to form the colorant.

2. A process according to claim 1 wherein the base is a trialkyl amine or an inorganic base.

3. A process according to claim 1 wherein the base is triethylamine, tripropylamine, tributylamine, piperidine, 1,4-diazabicyclo[2.2.2]octane, lithium hydroxide, sodium hydroxide, potassium hydroxide, lithium carbonate, sodium carbonate, potassium carbonate, lithium hydride, sodium hydride, potassium hydride, lithium alkoxide, sodium alkoxide, potassium alkoxide, or mixtures thereof.

4. A process according to claim 1 wherein the base is potassium carbonate.

5. A process according to claim 1 wherein the reaction of 3-n-pentadecylphenol with 4-nitrophthalonitrile is carried out in a solvent.

6. A process according to claim 5 wherein the solvent is methanol, ethanol, propanol, butanol, dioxane, acetone, toluene, nitrobenzene, dimethyl formamide, dimethyl sulfoxide, 1-methyl-2-pyrrolidinone, 1-cyclohexyl-2-pyrrolidinone, sulfolane, or mixtures thereof.

7. A process according to claim 5 wherein the solvent is present in an amount of at least about 0.5 parts by weight solvent per every 1 part by weight 3-n-pentadecylphenol, and wherein the solvent is present in an amount of no more than about 20 parts by weight solvent per every 1 part by weight m-n-pentadecylphenol.

8. A process according to claim 1 wherein the reaction of 3-n-pentadecylphenol with 4-nitrophthalonitrile is carried out at a temperature of at least about 30° C., and wherein the reaction of 3-n-pentadecylphenol with 4-nitrophthalonitrile is carried out at a temperature of no more than about 150° C.

9. A process according to claim 1 wherein the 3-n-pentadecylphenol and the base are admixed and subjected to heating prior to admixing the 3-n-pentadecylphenol with the 4-phthalonitrile.

10. A process according to claim 1 wherein the reaction of 3-n-pentadecylphenol with 4-nitrophthalonitrile is carried out for a period of at least about 0.25 hour, and wherein the reaction of m-n-pentadecylphenol with 4-nitrophthalonitrile is carried out for a period of no more than about 24 hours.

11. A process according to claim 1 wherein the molar ratio of 3-n-pentadecylphenol to 4-nitrophthalonitrile is at least about 1:1, and wherein the molar ratio of 3-n-pentadecylphenol to 4-nitrophthalonitrile is no more than about 3:1.

12. A process according to claim 1 wherein the molar ratio of 3-n-pentadecylphenol to base is at least about 1:1, and wherein the molar ratio of 3-n-pentadecylphenol to base is no more than about 1.5:1.

13. A process according to claim 1 wherein the alkylarylether adduct of phthalonitrile is isolated prior to the reaction of the alkylarylether adduct of phthalonitrile with the metal compound, the ammonia-releasing compound, or the mixture thereof.

14. A process according to claim 13 wherein subsequent to isolation, the alkylarylether adduct of phthalonitrile is washed with at least one of water, a dilute acid, and a dilute base.

15. A process according to claim 1 wherein in step (b) the alkylarylether adduct of phthalonitrile is reacted with a metal compound.

16. A process according to claim 15 wherein the metal compound is of the formula $MX_n \cdot yH_2O$ wherein M is a metal atom, X is an anion, n is a number representing the valence of the metal, and y is an integer of from 0 to 10.

17. A process according to claim 16 wherein M is dilithium, disodium, dipotassium, beryllium, magnesium, calcium, strontium, barium, chromium, manganese, iron, cobalt, nickel, copper, zinc, tin, lead, cadmium, or mixtures thereof.

18. A process according to claim 15 wherein the metal salt is a copper salt, a nickel salt, a cobalt salt, a zinc salt, or a mixture thereof.

19. A process according to claim 15 wherein the metal compound is a copper salt.

20. A process according to claim 19 wherein the copper salt is anhydrous copper chloride, hydrated copper chloride, anhydrous copper acetate, hydrated copper acetate, anhydrous copper sulfate, hydrated copper sulfate, anhydrous copper nitrate, hydrated copper nitrate, anhydrous copper bromide, hydrated copper bromide, or mixtures thereof.

21. A process according to claim 15 wherein the reaction of the alkylarylether adduct of phthalonitrile with the metal compound is carried out in a solvent.

22. A process according to claim 21 wherein the solvent is ethylene glycol, amyl alcohol, hexanol, heptanol, tetralin, decalin, a refined mineral spirits solvent, xylene, tributyl amine, N,N-dimethylaniline, quinoline, 1-chloronaphthalene, a trialkanolamine, a monoalkyl dialkanolamine, a dialkyl monoalkanolamine, dimethylsulfoxide, N,N-dimethylformamide, N,N-dimethylacetamide, 1-methyl-2-pyrrolidinone, N-cyclohexyl-2-pyrrolidinone, sulfolane, or mixtures thereof.

23. A process according to claim 22 wherein the solvent is present in an amount of at least about 100 parts by weight solvent per every 60 parts by weight alkylarylether phthalonitrile adduct, and wherein the solvent is present in an amount of no more than about 100 parts by weight solvent per every 3 parts by weight alkylarylether phthalonitrile adduct.

24. A process according to claim 15 wherein the reaction of the alkylarylether adduct of phthalonitrile with the metal compound is carried out at a temperature of at least about 80° C., and wherein the reaction of the alkylarylether adduct of phthalonitrile with the metal compound is carried out at a temperature of no more than about 250° C.

25. A process according to claim 15 wherein the reaction of the alkylarylether adduct of phthalonitrile with the metal compound is carried out for a period of at least 1 hour, and wherein the reaction of the alkylarylether adduct of phthalonitrile with the metal compound is carried out for a period of no more than about 24 hours.

26. A process according to claim 15 wherein the molar ratio of alkylarylether phthalonitrile adduct to metal compound is at least about 2:1, and wherein the molar ratio of alkylarylether phthalonitrile adduct to metal compound is no more than about 10:1.

27. A process according to claim 15 wherein the reaction of the alkylarylether adduct of phthalonitrile with the metal compound is carried out in the presence of a catalyst or reaction promoter.

28. A process according to claim 27 wherein the catalyst or reaction promoter is a trialkanolamine, a dialkyl monoalkanolamine, a monoalkyl dialkanolamine, or a mixture thereof.

29. A process according to claim 28 wherein the dialkyl monoalkanolamines and monoalkyl dialkanolamines have alkyl groups with from 1 to about 6 carbon atoms and wherein the trialkanolamines, dialkyl monoalkanolamines, and monoalkyl dialkanolamines have alkanol groups with from about 2 to about 6 carbon atoms.

30. A process according to claim 27 wherein the catalyst or reaction promoter is 2-diethylaminoethanol, 2-dimethylaminoethanol, 2-dimethylamino-1-propanol, or mixtures thereof.

31. A process according to claim 27 wherein the catalyst or reaction promoter is an ammonia-releasing compound.

32. A process according to claim 31 wherein the catalyst or reaction promoter is ammonium carbonate, ammonium carbamate, ammonium bicarbonate, ammonium molybdate, urea, an ammonium salt of a mono- or dicarboxylic acid, or a mixture thereof.

33. A process according to claim 31 wherein the reaction of the alkylarylether phthalonitrile adduct with the metal compound takes place with a two stage temperature-warming profile wherein the reaction mixture is first heated to a first temperature and subsequently heated to a second temperature higher than the first temperature.

34. A process according to claim 33 wherein the first temperature is at least about 80° C., and wherein the first temperature is no more than about 140° C.

35. A process according to claim 33 wherein the reaction mixture is maintained at the first temperature for a period of at least about 0.25 hour, and wherein the reaction mixture is maintained at the first temperature for a period of no more than about 3 hours.

36. A process according to claim 33 wherein the second temperature is at least about 120° C., and wherein the second temperature is no more than about 250° C.

37. A process according to claim 33 wherein the reaction mixture is maintained at the second temperature for a period of at least about 1 hour, and wherein the reaction mixture is maintained at the second temperature for a period of no more than about 24 hours.

38. A process according to claim 27 wherein the catalyst or reaction promoter is a mixture of (a) a trialkanolamine, a dialkyl monoalkanolamine, a monoalkyl dialkanolamine, or a mixture thereof, and (b) an ammonia-releasing compound.

39. A process according to claim 27 wherein the molar ratio of catalyst or reaction promoter to metal compound is at least about 0.1:1, and wherein the molar ratio of catalyst or reaction promoter to metal compound is no more than about 10:1.

40. A process according to claim 15 wherein M is dihydrogen, wherein the metal compound is an alkali metal compound, and wherein the product of step (b) is subsequently reacted with an acid.

41. A process according to claim 40 wherein the acid is hydrochloric acid, phosphoric acid, sulfuric acid, nitric acid, an alkylsulfonic acid, an arylsulfonic acid, an alkylarylsulfonic acid, an arylalkylsulfonic acid, an alkylcarboxylic acid, an arylcarboxylic acid, an alkylarylcarboxylic acid, an arylalkylcarboxylic acid, or mixtures thereof.

42. A process according to claim 40 wherein the acid is present in a water or alcohol solution in a concentration of at least about 1 percent by weight acid, and wherein the acid is present in a water or alcohol solution in a concentration of no more than about 10 percent by weight acid.

43. A process according to claim 1 wherein M is dihydrogen and wherein in step (b) the alkylarylether adduct of phthalonitrile is reacted with an ammonia-releasing compound in the presence of a dialkyl monoalkanolamine solvent.

44. A process according to claim 43 wherein the dialkyl monoalkanolamine solvent is 2-dimethylaminoethanol, 2-diethylaminoethanol, 2-dimethylamino-1-propanol, or mixtures thereof.

45. A process according to claim 43 wherein the ratio by weight of 4-(3-pentadecyl)phenoxyphthalonitrile to dialkyl monoalkanolamine solvent is at least about 10:80, and wherein the ratio by weight of 4-(3-pentadecyl) phenoxyphthalonitrile to dialkyl monoalkanolamine solvent is no more than about 60:40.

46. A process according to claim 43 wherein the ammonia-releasing compound is ammonium carbonate, ammonium carbamate, ammonium bicarbonate, ammonium molybdate, urea, an ammonium salt of a mono- or dicarboxylic acid, or a mixture thereof.

47. A process according to claim 43 wherein the molar ratio of ammonia-releasing compound to alkylarylether adduct of phthalonitrile is at least about 0.1 molar equivalent ammonia-releasing compound per every 1 molar equivalent of alkylarylether adduct of phthalonitrile, and wherein the molar ratio of ammonia-releasing compound to alkylarylether adduct of phthalonitrile is no more than about 5 molar equivalents ammonia-releasing compound per every 1 molar equivalent of alkylarylether adduct of phthalonitrile.

48. A process according to claim 43 wherein the reaction of the alkylarylether phthalonitrile adduct with the ammonia-releasing compound takes place with a two stage temperature-warming profile wherein the reaction mixture is first heated to a first temperature and subsequently heated to a second temperature higher than the first temperature.

49. A process according to claim 48 wherein the first temperature is at least about 50° C., and wherein the first temperature is no more than about 130° C.

50. A process according to claim 48 wherein the reaction mixture is maintained at the first temperature for a period of at least about 10 minutes, and wherein the reaction mixture is maintained at the first temperature for a period of no more than about 120 minutes.

51. A process according to claim 48 wherein the second temperature is at least about 120° C., and wherein the second temperature is no more than about 200° C.

52. A process according to claim 48 wherein the reaction mixture is maintained at the second temperature for a period of at least about 1 hour, and wherein the reaction mixture is maintained at the second temperature for a period of no more than about 24 hours.

* * * * *